(12) United States Patent
Eisen

(10) Patent No.: US 6,858,716 B2
(45) Date of Patent: Feb. 22, 2005

(54) DROSOPHILA RECOMBINATION-ASSOCIATED PROTEIN AND METHODS FOR USE

(75) Inventor: Andrew Eisen, Rockville, MD (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 38 days.

(21) Appl. No.: 10/353,174

(22) Filed: Jan. 28, 2003

(65) Prior Publication Data

US 2003/0144495 A1 Jul. 31, 2003

Related U.S. Application Data

(63) Continuation of application No. 09/621,377, filed on Jul. 21, 2000, now Pat. No. 6,534,643.
(60) Provisional application No. 60/144,736, filed on Jul. 21, 1999.

(51) Int. Cl.[7] .................. C07H 21/02; C07H 21/04; C12Q 1/68
(52) U.S. Cl. ...................... 536/23.1; 435/320.1
(58) Field of Search .................. 536/23.1; 435/320.1

(56) References Cited

U.S. PATENT DOCUMENTS 6,534,643 B1 * 3/2003 Eisen .................. 536/23.5

OTHER PUBLICATIONS

Lodish et al. Molecular Cell Biology 3 Ed. p. 104–108 1995.*
Baumann, Peter, et al., "Human Rad51 Protein Promotes ATP–Dependent Homologous Pairing and Strand Transfer Reactions in Vitro", *Cell*, 87:757–766 (1996).
Benson, Fiona E, et al., "Synergistic Actions of Rad51 and Rad52 in Recombination and DNA Repair", *Nature*, 391:401–403 (1998).
Bosher, Julia M, et al., "RNA Interference: Genetic Wand and Genetic Watchdog", *Nature Cell Biology*, 2:E31–E36 (2000).
Bushman, Frederic D. et al., "Domains of the Integrase Protein of Human Immunodeficiency Virus Type 1 Responsible for Polynucleotidyl Transfer and Zinc Binding", *Proc. Natl. Acad. Sci.* USA, 90:3428–3432 (1993).
Camerini–Otero, R. Daniel, et al., "Homologous Recombination Proteins in Prokaryotes and Eukaryotes", *Annu. Rev. Genetics*, 29:509–552 (1995).

(List continued on next page.)

Primary Examiner—James Ketter
Assistant Examiner—Konstantina Katcheves
(74) Attorney, Agent, or Firm—Darby & Darby

(57) ABSTRACT

The invention encompasses Drosophila Recombination Associated Protein (DRAP) isolated from *D. melanogaster* and a nucleic acid sequence encoding DRAP. The Drosophila Recombination Associated Protein, its homologues from other organisms or active peptides derived therefrom, as well as DNA encoding such protein are useful for homology-dependent pairing of three DNA strands. The combination of strand-transfer and topoisomerase activities associated with DRAP permits directed pairing and cleavage at defined site(s) within DNA. This in turn makes possible the isolation and/or removal of a defined segment of DNA. DRAP is also useful in cloning, genomic cloning and gene mapping, in promoting gene disruptions or "knockout" mutations, in carrying out targeted mutagenesis of specific genes and in generating transgenic animals. The invention further encompasses a method for experimental and therapeutic application of DRAP driven knockouts or other modifications of genes responsible for genetic diseases as well as the use of DRAP driven genetic manipulation of genes in gene therapy.

2 Claims, 25 Drawing Sheets

DRAP Complete cDNA Clone Insert

```
agcgattacg gtagagatat ggtaatgcaa cggtggatgt gaactccttg    50
gtttgcggtg aatgcgttca acggtggatc ttcgcttgca cctttcgcga   100
tagacgacat acggatacag atacagatac agaatggcct ccaacaacag   150
tagtaccacc gatctggaca gccaggtcaa tgtgcaggat ttgcccataa   200
cgttcaaggt gaagtacatt ggttccgaag tggcacgtgg cttatgggac   250
attaagtata cgcgtcgtcc ggttgacata atggtgggcg tggccaagaa   300
cctgccgccc aataaggtgc tgcccaactg cgaactgaag gtgtccaccg   350
acggagtcca gctggagatc atatcgccaa aggccagcat caatcactgg   400
agctatccca tcgacacgat ctcgtatggc gttcaggacc tggtctacac   450
aagggtcttt gccatgatcg tggtgaagga cgagtcgagt ccgcatccct   500
ttgaggttca cgccttcgtg tgcgacagtc gtgcgatggc gcggaagttg   550
accttttgccc tggccggccg ccttccagga ttactcgcga cgggtcaagg   600
aggcaaccgg tgaggaggag ggcgaggcca cgcccagcga cactattaca   650
cccacgcgac acaagttcgc catcgatctg cgaacgccgg agaaatccag   700
gctggcgaac tgagcagga aacggaggcg tagttatcct ggtgatcctg   750
cgttggctcc gtcaatgaga tgtgatgtgt tagttactta acgtccagtg   800
```

OTHER PUBLICATIONS

Chen, Frances E, et al., "Crystal Structure of p50/p65 Heterodimer of Transcription Factor NF-$_\kappa$B Bound to DNA", *Nature*, 391:410–413 (1998).

Cheng, Chonghui, et al., "Conservation of Structure and Mechanism Between Eukaryotic Topoisomerase 1 and Site-Specific Recombinases",Cell, 92:841–850 (1998).

Drees, Becky L, "Progress and Variations in Two-Hybrid and Three-Hybrid Technologies", *Current Opinion in Chemical Biology.*, 3:64–70 (1999).

Dunderdale, Hazel J. et al., "Formation and Resolution of Recombination Intermediates by E. coli RecA and RuvC Proteins", *Nature*, 354:506–510 (1991).

Eisen, Andrew, et al., "A Recombinase from Drosophila Melanogaster Embryos", *Proc. Natl. Acad. Sci. USA*, 85:7481–7485 (1988).

Eggleston, Angela K, et al., "In Vitro Reconstitution of the Late Steps of Genetic Recombination in E. coli", Cell, 89:607–617 (1997).

Feng, Yu. et al., "HIV–1 Entry Cofactor: Functional cDNA Cloning of a Seven–Transmembrane, G Protein–Coupled Receptor", *Science*, 272:872–877 (1996).

Ferrin, Lance J, et al., "Long-Range Mapping of Gaps and Telomeres with RECA–Assisted Restriction Endonuclease (RARE) Cleavage" *Nature Genetics*. 6:379–383 (1994).

Ferrin, Lance J "Manipulating and Mapping DNA with RecA–Assisted Restriction Endonuclease (RARE) Cleavage", Genetic Engineering, 17:21–30 (1995).

Gangloff, S, et al., "Transcription, Topoisomerases and Recombination",Experientia, 50: 261–269 (1994).

Grindley, Nigel., D.F, et al., "DNA Transposition: From a Black Box to a Color Monitor", *Cell*, 83:1063–1066 (1995).

Heyer, W.D., "The Search for the Right Partner: Homologous Pairing and DNA Strand Exchange Proteins in Eukaryotes", Experientia, 50:223–233 (1994).

Hunter, Craig P, et al., "Hox Gene Expression In a Single Caenorhabditis elegans Cell Is Regulated By a Caudal Homolog and Intercellular Signals That Inhibit WNT Signaling", *Development*, 126:805–814 (1999).

New, James H, et al., "Rad52 Protein Stimulates DNA Strand Exchange by Rad51 and Replication Protein A", *Nature*, 391:407–409 (1998).

Nomura, Tatsuji, "Practical Development of Genetically Engineered Animals as Human Disease Models", *Laboratory Animal Science*, 47:113–117 (1997).

Plasterk, Ronald H.A, "Molecular Mechanisms of Transposition and Its Control", *Cell*, 74:781–786 (1993).

Rice, Phoebe, et al., "Structure of the Bacteriophage Mu Transposase Core: A Common Structural Motif for DNA Transposition and Retroviral Integration", *Cell*, 82:209–220 (1995).

Sherratt, David J, et al., "Conserved Themes but Novel Activities in Recombinases and Topoisomerases", Cell, 93:149–152 (1998).

Shinohara, Akira, et al., "Stimulation by Rad52 of Yeast Rad51–Mediated Recombination", *Nature*, 391:404–406 (1998).

Torres, Miguel, "The Use of Embryonic Stem Cells for the Genetic Manipulation of the Mouse", *Current Topics in Development Biology.*, 36:99–114 (1998).

Voloshin, Oleg N, "Homologous DNA Pairing Promoted by a 20–Amino Acid Peptide Derived from RecA", *Science*, 272:868–871 (1996).

Wang, James C, et al., "The Role of DNA Topoisomerase in Recombination and Genome Stability: A Double–Edged Sword?", *Cell*, 62:403–406 (1990).

Yancey–Wrona, Janet E, et al., "The Search for DNA Homology Does Not Limit Stable Homologous Pairing Promoted by RecA Protein", *Current Biology*, 5:1149–1158 (1995).

Adams, M.D. et al., *Science*, 287:2185–2195, Mar. 24, 2000.

Hendrix, R.W. et al., *Proc. Natl. Acad. Sci. USA*, 96:2191–2197, 03/99.

Turner, et al., *Cell*, 77:297–306 (1994).

Furuya, et al., J.Bacteriol , 178:1491–1497 (1996).

Yoshiura, et al., Database SPTREMBL, AC 096026, May 1, 1999.

Hendrix, et al., Database SPTREMBL AC Q9ZXA7, May 1, 1999.

Adams et al. (2000). The genome of Drosophila melanogaster, *Science*, 287:2185 (ABSTRACT and Genbank entry NM_ 160814).

\* cited by examiner

FIG. 1A

DRAP Complete cDNA Clone Insert

```
agcgattacg gtagagatat ggtaatgcaa cggtggatgt gaactccttg     50
gtttgcggtg aatgcgttca acggtggatc acgtggatc ttcgcttgca cctttcgcga    100
tagacgacat acggatacag atacagatac agaatggcct ccaacaacag    150
tagtaccacc gatctggaca gccagtgtca tgtggaggat ttgcccataa    200
cgttcaaggt gaagtacatt ggttccgaag tggcacgtgg cttatgggc    250
attaagtata cgccgtcgtc ggttgacata atgggtgggcg tggccaagaa    300
cctgccgccc aataaggtgc tgcccaactg cgaactgaag gtgtccaccg    350
acggagtcca gctggagatc atatcgccaa aggccagcat caatcactgg    400
agctatccca tcgacacgat ctcgtatggc gttcaggacc tggtctacac    450
aagggtcttt gccatgatcg tggtgaagga cgagtcgagt ccgcatccct    500
ttgaggttca cgcctttcgtg tgccttcgtg tgcgatggc gcggaagttg    550
acctttgccc tggccgggccg cccttccagga ttactcgcga cgggtcaagg    600
aggcaaccgg tgaggaggag ggcgaggcca cgcccagcga cactattaca    650
cccacgcgac acaagttcgc catcgatctg cgaacgccgg agaaatccag    700
gctggcgaac tggagcagga aacggaggcg tagttatcct ggtgatcctg    750
cgttggctcc gtcaatgaga tgtgatgtgt tagttactta acgtccagtg    800
```

```
ttcactgtat ctgtaaattg tggttctctc acctggtagt tgcctcatac    850
agctaattac ccaagcccta agtgttaata cgatttgtaa acgatttcta    900
aaataaatta cgaatatggt atgtttggct atttgaattg ggctacaacc    950
tgttgatatg ccacttggca aaaaaaaaa acgccagcac caattctttt   1000
acttctgttt cttgtgaccg acataaaaga tgcaccaaag ctgctattcc   1050
accagcgttc tttattccac gcttgttttc atcattttgt cttccgtaag   1100
ataaattacg taaagcacca caggcatttt tatgtatttc tggagaatca   1150
taagatagca gtcgaactaa tggtggtata cctcccagag atcttgtacg   1200
ttgcttgttt ggatcatcca tgtagcacaa atgctgtaga taggctgctg   1250
cattagcttt tatagcacta ctcgggttgc ttaaaaagct tattacttct   1300
gaaagatttg gatcccgcca tctcattgta gaacaaatat catttcctga   1350
tccttcaatg taatcatcct tttcttcc                           1378
```

Longest ORF                               nt 104 - 610

Probable Start Codon                      nt 134

CDS Expressed as Recombinant Protein      nt <u>134 - 610</u>

DRAP Coding Sequence - Restriction Map

FIG. 2B

```
194 ---------+---------+---------+---------+---------+---------+ 253
    gggtattgcaagttccacttcatgtaaccaagcttcaccgtgaccgaataccccgtaa
     P  I  T  F  K  V  K  Y  I  G  S  E  V  A  R  G  L  W  G  I  -

B                                        B
          s                                M       s
          t A                              s     B b p
          1 1M                             c     b v M
          1 0 I l                          I     I I I
          1 7 Iu
            I II
             / aagtatacgcgtcgtccggttgacataatgtgggcgtggccaagaacctgccgcccaat
254 ---------+---------+---------+---------+---------+---------+ 313
    ttcatatgcagcaggccaactgtattaccacccgcaccgttcttggacggcgggtta
     K  Y  T  R  R  P  V  D  I  M  V  G  V  A  K  N  L  P  P  N  -

```
           B
314 aaggtgctgcccaactgcgaactgaaggtgtccaccgacgacggagtccagctggagatcata 373
    ----+---------+---------+---------+---------+---------+---------+----
    ttccacgacgggttgacgcttgacttccacaggtcgtgctgctgcctcaggtcgacctctagtat
     K  V  L  P  N  C  E  L  K  V  S  T  D  G  V  Q  L  E  I  I
                                    T
                                    Bs
                                    sp
                                    rR
                                    II
                                    /
                                                                           B
374 tcgccaaaggccagcatcaatcactgagctatcccatcgacacgatctcgtatggcgtt 433
    ----+---------+---------+---------+---------+---------+---------+----
    agcggtttccggtcgtagttagtgactcgataggggtagctgtgctagagcataccgcaa
     S  P  K  A  S  I  N  H  W  S  Y  P  I  D  T  I  S  Y  G  V
                                                                           C
```

FIG. 2D

```
           S  P  K  A  S  I  N  H  W  S  Y  P  I  D  T  I  S  Y  G  V
           E     S
           c     s
           oP    s e                                    F
           AOsAaS8           N                          o
           vlplue6           l                          k
           a05w9x4           a     I                    I
           I9IN6A7           I     I
           IIIIIII           I     I
           // ///
          caggacctggtctacacaagggtctttgccatgatcgtggtgaaggacgagtcgagtccg
    434   -----+---------+---------+---------+---------+---------+---  493
          gtcctggaccagatgtgttcccagaaacgtactagcaccacttcctgctcagctcaggc Q  D  L  V  Y  T  R  V  F  A  M  I  V  V  K  D  E  S  S  P
                                                        H  B
                                                        h  c
                                                        a  g
                                                        I  I
          catccctttgaggttcacgccttcgtgtgcgacagtcgtgcgatggcgcggaagttgacc
```

FIG. 2E

```
494 ---------+---------+---------+---------+---------+---------+ 553
    gtaggaaactccaagtgcggaagcacacgctgtcagcacgctaccgcgccttcaactgg

H  P  F  E  V  H  A  F  V  C  D  S  R  A  M  A  R  K  L  T

N                                    B           P
         B    g     B                               s           i
         s    o     E Fs                        N   c           n
         a    A     a si                        r   G           A
         J    I     g eE                        u   I           I
         I    V     I II                        I   I
    tttgccctggccgcgccttccaggattactcgcgggtcaaggaggcaaccggtga
554 ---------+---------+---------+---------+---------+---------+ 613
    aaacgggaccggcgcggaaggtcctaatgagcgctgcccagttcctccgttggccact

F  A  L  A  G  R  L  P  G  L  L  A  T  G  Q  G  G  N  R  * ggaggag
614 -------+ 620
    cctcctc

G  G
```

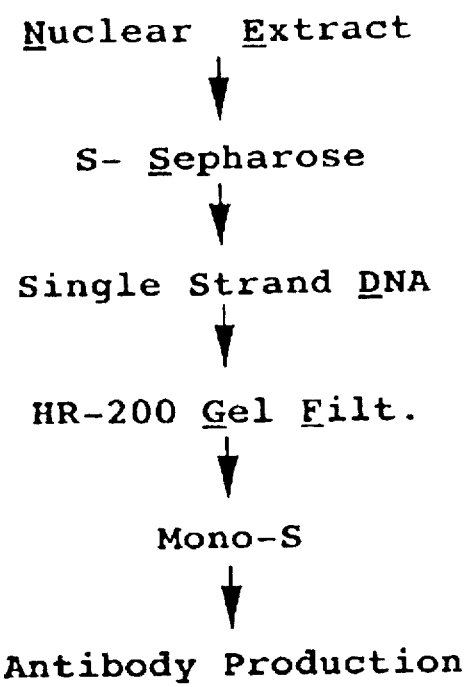
FIG. 3A
FIG. 3B
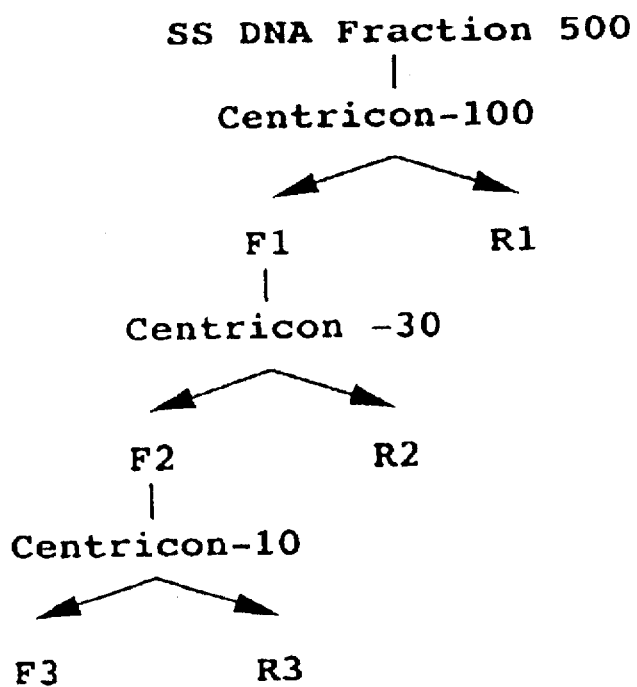

GF:
28   #28
674   A-7
PAb   MAb

— 95

— 45

— 30

— 20
KDa
A7--Eluate

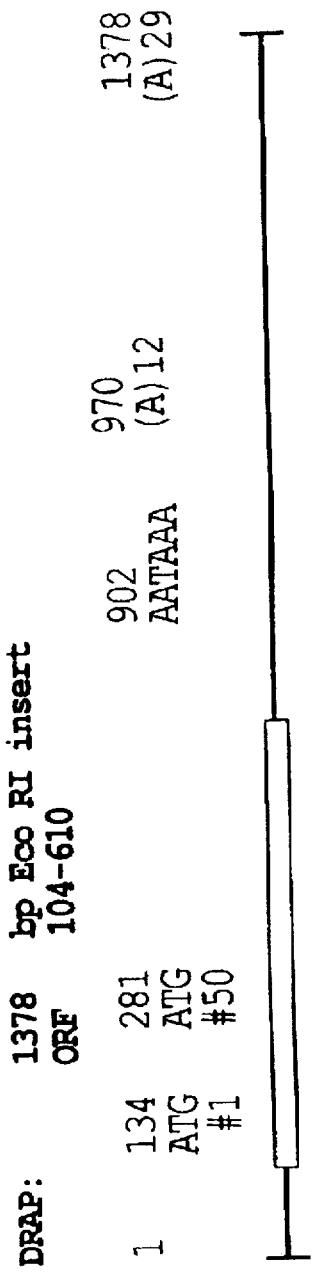

FIG. 4C

| Potential | D1----(30 to 70)----D2----(35±)----E1 | Motifs |
|---|---|---|
| AA#s | (10 or 12)----(36 to 38)----48----(30)----78 | |
| | 19 ) ---( 54 )----(44)----117 | |
| | (19 or 48)----(46 to 75)----94----(30)----124 | |

FIG. 4D

| | | | | | |
|---|---|---|---|---|---|
| Rad 51 | Mouse - Human | L L I V | - D - | S | |
| Rad 51 | Yeast | L I V V | - D - | S | |
| DCM 1 | Yeast | L I V V | - D - | S | |
| RecA | E. Coli | V I V V | - D - | S | |
| Drosophila DRAP | | M I V V K | D E S | S P | |
| FLP Recombinase | | M I A L K | D E T N P | | |
| T4 Gene 32 Protein | | I L V V K | D P A A P | | |
| | | M I A V - | D V E M G E | | |
| | | K - GFS S E | | | |
| Human Topoisomerase I | | I K D E - - P | | | |
| | | K D G S S E | | | |
| | | GFS S P | | | |

E. coli Lysate
↓
Ni NTA
↓
Phosphocellulose
↓
Sephadex 75
↓
Concentrate / Assay

| Targeted Transgenics | | |
|---|---|---|

| Gene | Oligo (No Phenotype) | Oligo + DRAP (Molar Ratio - Protein : Oligo) | |
|---|---|---|---|
| 1. N - myc (Exon 1) | 16 | Low (1:1)<br>High (100:1) | 60 OK<br>4 Alive<br>11 Stillborn |
| 2. β1 globin (Ala --> Val) | 7 | High (100:1) | 10 OK<br>5 Runts<br>  4 OK<br>  1 Sickly |
| 3. Agouti | 11 | High (100:1) | 8 OK |

FIG. 12A    Murine c-Kit Exon 17

```
           18 bp RFPL
          |<---------------->|
Intron:
gga cag
========

DpnI
                                                        Sau3AI
                                                        EciI
                                                        AciI
                 BseRI                                  BscGI
                 ScrFI                                  MnlI
                 CviJI                                  MnlI                    AlwI
                 EcoRII                Sthl32I          BbvI
                 Fnu4HI                BbvI
                 TseI
cDNA:  tgtattcacagagatttggcagccaggaatatcctcactcacgggcggatcacaaag
2384   ======>+---------+---------+---------+---------+---------+
       acataagtgtctctaaaccgtcggtccttataggagtgagtgcccgcctagtgttc C   I   H   R   D   L   A   A   R   N   I   L   L   T   H   G   R   I   T   K    -

CviJI
                  BsmAI                         Tsp509I
                  Cac8I                         NspV
                  BfaI                          TaqI
                  CviJI                         HinfI        BsaAI
                  NheI                          TfiI         MaeII
       atttgcgattcggctagccagagacatcaggaattgattcgaattacgtggtcaaaggaaatg
Sthl32I --<======+---------+---------+---------+---------+---------+
       taaacgctaaagcccgatcggtctctgtagtcttactaagcttaatgcaccagtttcctttac
2444

W42 Mutation

```
                                                        DpnI
                                                        Sau3AI
                                                        EciI
                                                        AciI
                                          BscGI
                                          MnlI
          BseRI
          ScrFI
          CviJI             Sth132I
          EcoRII      BbvI                                          AlwI
    ApoI  Fnu4HI
    Tsp509I  TseI tgtattcacagaaatttggcagccaggaatatcctcactcacggggcggatcacaaag
 1 ----+----+----+----+----+----+----+----+----+----+----+ 60
   acataagtgtctttaaaccgtcggtccttataggagtgagtgcccgcctagtgttc

C I H R N L A A R N I L L T H G R I T K  -
                 N
```

Mutation & RFLP

Underline: Potential Mutagenic Oligo
====> <==== Potential PCR Primers for RFLP Analysis

US 6,858,716 B2

DROSOPHILA RECOMBINATION-ASSOCIATED PROTEIN AND METHODS FOR USE

RELATED APPLICATIONS

This application is a continuation of application Ser. No. 09/621,377, filed Jul. 21, 2000, now U.S, Pat. No. 6,534,643 and claims the benefit of priority under 35 U.S.C. §119(e) of provisional application Ser. No. 60/144,736, filed Jul. 21, 1999. Each of the foregoing applications is hereby incorporated by reference in its entirety.

FIELD OF THE INVENTION

This invention encompasses the Drosophila Recombination Associated Protein (DRAP), nucleic acid sequences encoding DRAP, and methods of using DRAP.

BACKGROUND

One common method for introducing exogenous genes in eukaryotic cells and organisms is by direct transfection. Transfection is relatively efficient but genomic integration tends to be random and regulation of gene expression can be difficult. Various strategies have been developed to enhance the control of transgene expression, limit expression to a specific tissue or link expression to a specific time during development in transgenic animals. The direct transgenic approach suffers primarily from an inability to directly modify a specific genetic locus.

Another approach for introducing exogenous genes into eukaryotic cells utilizes homologous recombination directed at a specific locus in specialized embryonic stem cells. A number of genes and gene products that participate in general and site-specific recombination in viruses, prokaryotes and eukaryotes have been identified. (Camerini-Otero, R. D., et al., Ann. Rev. Genetics, 1995, 29:509–522.) These gene products and/or proteins encoded by these genes have proven useful in the molecular genetic manipulation of DNA in vitro and in vivo with applications in cloning, gene mapping and manipulation of genomes in living organisms. (Grindley, N. D., et al., 1995, Cell 83: 1063–1066; and Wang, J. C., et al., 1990, Cell 62: 403–406.) The use of such proteins in these applications relies upon their activity in homologous recombination.

Homologous recombination is routinely used to create "knock out" mutations in the production of mutant animals. (Nomura, T., 1997, Lab Anim. Sci. 47: 113–117; and Torres, M., 1998, Cur. Top. Dev. Biol. 36: 99–114.) This approach results in gene-directed, i.e. sequence directed, insertions that "knock out" gene function to produce such mutations. Although this approach is generally an inefficient process, selection methods and screening permit facilitated identification of cells bearing specific genomic modifications. The enzymatic machinery that completes this low efficiency process in specialized embryonic stem cells is unknown. It would thus be beneficial to identify one or a number of genes or gene products involved so that homologous recombination could be performed with a higher efficiency. Such site specific homologous recombination might prove useful for therapeutic purposes. The use of these specific genes and/or gene products could improve the efficiency of the knock-out process and extend the range of cell types where homologous recombination could be accomplished.

It would thus be highly desirable to develop a method for efficient, homology directed genome modification that would permit modification of genes ranging from knockouts to subtle modifications. Such methods would rely upon the use of an efficient homology dependent DNA pairing protein capable of directing a mutagenic oligonucleotide to its cognate gene within a complex genome. The aim of this approach would be to promote DNA strand exchange and force a gene conversion event that can be identified at the molecular level and is heritable. There are several, general, homology-dependent strand transferases that might be suitable for such a purpose that have been used for related purposes in vitro (e.g., the RARE technique). (Ferrin, L. J. et al., Nature Genetics, 1994, 6:379–383; and Ferrin, L. J., Genet. Eng., 1995, 17:21–30.

General recombinases currently used in the promotion of DNA strand transfers and gene conversions include UV Sensitive X ("UVSX") from T4 phage, Recombination Protein A ("RecA") from *E. coli* or RecA-derived peptides, or Radiation Induced Mutant 51 ("RAD51 ") from yeast or RAD 51 homologues from Drosophila, mouse and human. These proteins are each part of a large super-family of recombination-related proteins. These recombinases typically require accessory proteins such as Single Strand Binding Protein ("SSB"), Replication Protein A ("RPA") and Radiation Induced Mutant 52 ("RAD 52") in order to achieve maximal efficiency. There are also a host of site directed recombinases (of the integrase and resolvase superfamilies) that might be modified for such a purpose.

Drosophila embryos provide a rich source of enzymes that are involved in homologous recombination. (Eisen, A., et al, 1988, PNAS 85:7481–85.) It was shown that purified protein fractions possessed an efficient ATP-independent, homology-dependent strand transferase activity similar to RecA. The active fractions appeared to work catalytically as opposed to stoichiometrically. (Eisen, A. et al., 1988.) The Drosophila embryonic cells are rapidly dividing and thus provide a large quantity of enzymes involved in mitotic recombination and DNA processing. A similar potent homology-dependent strand transferase activity was demonstrated to be present in nuclear extracts from Drosophila. (Eisen, A. et al., 1988.) The apparent catalytic nature of this Drosophila protein activity distinguishes it from most general recombinases, typified by proteins in the RecA/Rad 51 superfamily of gene products which operate in a stoichiometric fashion (Camerini-Otero, R. D., et al., 1995; and Yancey-Wrona, J. E., et al., 1995, Current Biol. 5: 1149–1158; Baumann, P., et al., 1996, Cell 87: 757–766; Benson, F. E., et al., 1998, Nature 391: 401–404; Shinohara, A., et al., 1998, Nature 391: 404–407; New, J. H., et al., 1998, Nature 391: 407–410; Plasterk, R. H. A., 1993, Cell 74:781–786; and O. N. Voloshin, O. N., et al., 1996, Science 272: 868–872.) The unique Drosophila homology-dependent strand transferase activity offers certain theoretical advantages for performing high efficiency gene targeting. It would thus be advantageous to utilize this Drosophila activity in the promotion of homologous recombination and homology directed gene conversion.

SUMMARY OF THE INVENTION

The present invention provides an isolated cDNA clone containing the coding region for Drosophila Recombination Associated Protein (DRAP) [SEQ ID NO: 1], a DNA encoding DRAP corresponding to nt 134–610 of the isolated cDNA clone [SEQ ID NO: 2] and the longest Open Reading Frame (ORF) contained within the isolated cDNA clone sequence which corresponds to nt 104–610 of the isolated cDNA clone [SEQ ID NO: 3] (see FIGS. 1A–B). The invention also provides an isolated DRAP polypeptide as depicted in [SEQ ID NO: 4], as well as antigenic peptides, examples of which are defined by [SEQ ID NO: 5] [SEQ ID NO: 6] and [SEQ ID NO: 7] (see FIGS. 2A–E and 4B). The invention further provides DNA vectors and transformed cells suitable for recombinant expression of DRAP.

The Drosophila Recombination Associated Protein, its homologues from other organisms or active peptides derived therefrom, as well as DNA encoding such protein are useful for homology-dependent pairing of three DNA strands. The combination of strand-transfer and topoisomerase activities associated with DRAP permits directed pairing and cleavage at defined site(s) within DNA. This in turn makes possible the isolation and/or removal of a defined segment of DNA. DRAP is also useful in cloning, genomic cloning and gene mapping.

DRAP is also useful in promoting gene disruptions or "knockout" mutations, carrying out targeted mutagenesis of specific genes and in generating transgenic animals.

Thus, in one aspect, the present invention provides methods for DNA cloning, gene isolation and gene mapping.

In another aspect, the invention provides a method for targeted mutagenesis.

In yet a further aspect, the invention provides a method for experimental and therapeutic application of DRAP driven knockouts or other modifications of genes responsible for genetic diseases and the use of DRAP driven genetic manipulation of genes in gene therapy.

These and other aspects of the present invention will be apparent to those of ordinary skill in the art in light of the present description, claims and drawings.

BRIEF DESCRIPTION OF THE DRAWINGS

FIGS. 1A–B depicts the nucleotide sequence of an isolated cDNA clone containing the coding region for DRAP [SEQ ID NO: 1], a DNA encoding DRAP corresponding to nt 134–610 of the cDNA clone [SEQ ID NO: 2] and the longest Open Reading Frame (ORF) in the cDNA sequence corresponding to nt 104–610 of the cDNA clone [SEQ ID NO: 3].

FIGS. 2A–E depicts the nucleotide sequence [SEQ ID NO: 2] for DRAP, a restriction map of the nucleotide sequence and the corresponding amino acid sequence for the DRAP protein [SEQ ID NO: 4].

FIG. 3A depicts a schematic outline of the purification protocol used to purify a strand transferase activity from Drosophila nuclear extracts.

FIG. 3B depicts a schematic outline of the purification of fractions by elution from a single stranded (SS) DNA agarose column.

FIG. 4A depicts the cDNA for the DRAP protein.

FIG. 4B depicts the mature DRAP protein [SEQ ID NO:4] with the probable start site corresponding to the Met in the 11th codon position of the cDNA ORF (set as amino acid #1) with the mature protein being 159 amino acids long resulting in a protein of approximately 20 kDa. The numbered shaded regions depict the three most hydrophilic antigenic peptides predicted. These peptides, numbered 1, 2 and 3 are identified as KDESSP [SEQ ID NO:5], TRRPVD [SEQ ID NO:6] and RAMARK [SEQ ID NO:7], respectively.

FIG. 4C depicts the canonical DDE motifs characteristic of transposases and retroviral integrases (potential motifs). The DRAP DDE motifs closest to the canonical form are indicated below the canonical form with the locations for the $D_1$, $D_2$ and $E_1$ amino acids, along with the span of intervening amino acids, provided in parentheses.

FIG. 4D depicts a new motif MIVVKDESSP [SEQ ID NO: 15] shared between DRAP and other recombination-related proteins as identified through cross reactivity with anti-DRAP antibodies and sequence comparison. Depicted are motif sequences from mouse and human RAD 51, LLIVDS [SEQ ID NO: 23]; yeast RAD 51 and DCM 1, LIVVDS [SEQ ID NO: 24]; E. coli REC A, VIVVDS [SEQ ID NO: 25]; FLP recombinase, MIALKDETNP [SEQ ID NO: 26]; T4 Gene 32 protein, ILVVKDPAAP [SEQ ID NO: 27], MIAVDVEMGE [SEQ ID NO: 28] and KGFSSE [SEQ ID NO: 29]; and human topoisomerase I, IKDEP [SEQ ID NO: 30], KDGSSE [SEQ ID NO: 31] and GFSSP [SEQ ID NO: 32].

FIGS. 12A–B depicts the murine c-kit Exon 17 cDNA sequence [SEQ ID NO: 8], the potential mutagenic oligonucleotide ("oligo") for the locus (underlined portion), namely, tgtattcacagagatttggcagccaggaata [SEQ ID NO: 9], PCR primers to be used in Restriction Fragment Length Polymorphism ("RFLP") analysis (see double arrows), namely ggacagtgtattcac [SEQ ID NO: 10] and ttgcgatttcgggctag [SEQ ID NO: 11], the DNA nucleotide sequence of the W42 mutation [SEQ ID NO:12], and the amino acid protein sequences corresponding to SEQ ID NO: 8 and 12, namely [SEQ ID NO: 13] and [SEQ ID NO: 14], respectively. The figure also provides restriction maps of the DNA sequences.

DETAILED DESCRIPTION OF THE INVENTION

Figure 2A:
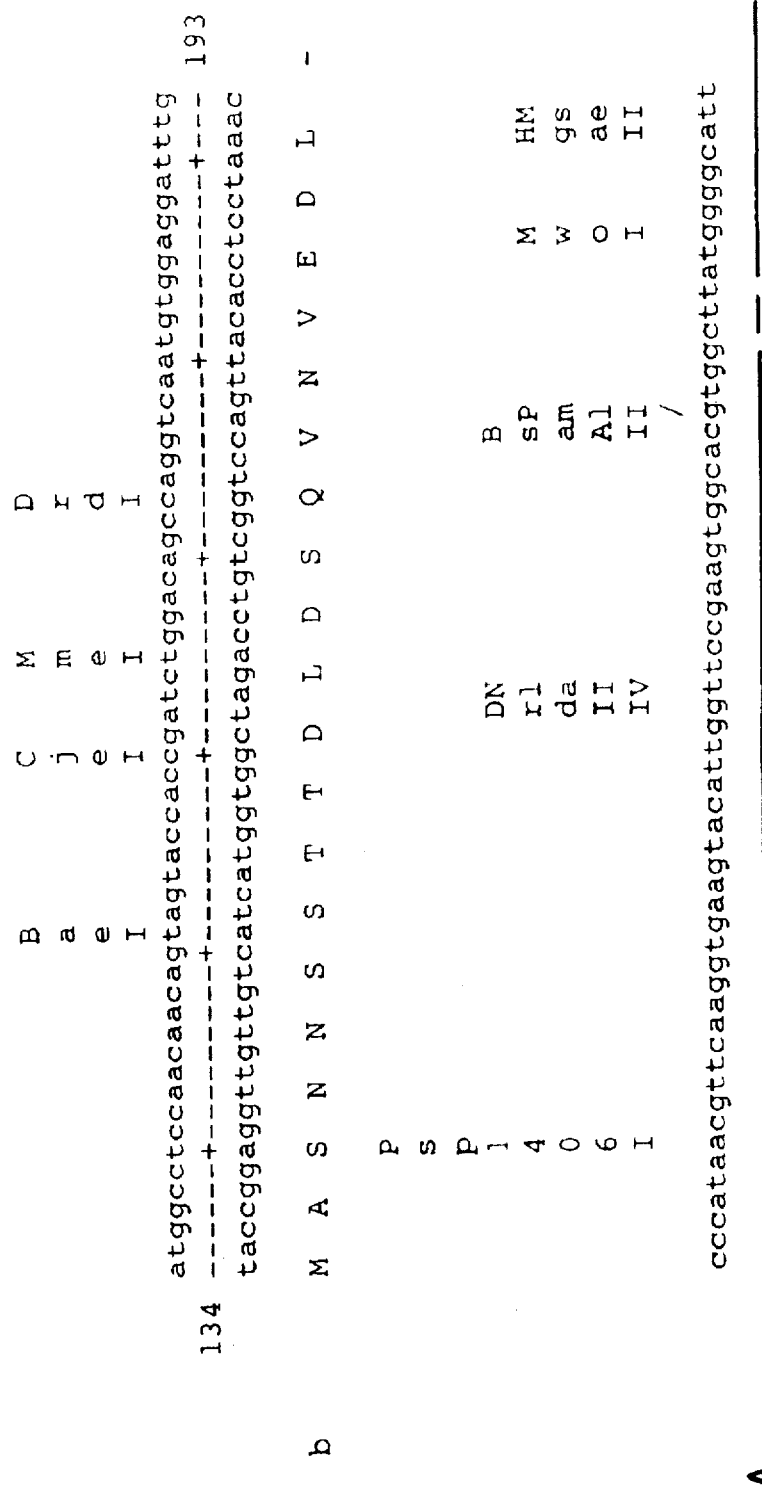

All patent applications, patents, and literature references cited in this specification are hereby incorporated by reference in their entirety. In case of conflict, the present description, including definitions, will control.

This invention is directed to an isolated nucleic acid which encodes a recombination-associated protein found in *Drosophila melanogaster* embryos, Drosophila Recombination Associated Protein (DRAP). The invention is also directed to the DRAP protein which exhibits both recombinase (homology-dependent strand transferase) and topoisomerase activity. This combination of properties provides for a protein useful in a number of activities including cloning or gene targeting protocols.

Definitions:

"Recombinase activity" as used herein refers to the promotion of homologous pairing and DNA strand exchange. Recombinases can be site-specific or general and can operate in a variety of biological contexts by a variety of biochemical mechanisms. Recombinase activity can also be promoted by smaller peptides derived from either native recombinase proteins or mutagenized peptides derived therefrom.

"Topoisomerase activity" as used herein refers to the ability of a protein to change the linking number of DNA. The "linking number" as used herein refers to the number of times the two strands of a closed DNA duplex cross over each other.

"Nucleic acid" or "polynucleotide" as used herein refer to purine- and pyrimidine-containing polymers of any length, either polyribonucleotides or polydeoxyribonucleotides or mixed polyribo-polydeoxyribo nucleotides. This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases.

An "isolated" polypeptide or nucleic acid is defined as one that is unaccompanied by at least some of the material with which it is associated in its natural state. Generally, an isolated polypeptide constitutes at least about 1%, preferably at least about 10%, and more preferably at least about 50% by weight of the total protein in a given sample. Included in the polypeptide weight are alternative forms such as differentially glycosylated or phosphorylated or otherwise post-translationally modified forms. An "isolated" nucleic acid sequence is present as other than a naturally occurring chromosome or transcript in its natural state and typically is removed from at least some of the proteins with which it is normally associated on a natural chromosome. A "partially pure" nucleotide sequence constitutes at least about 5%, preferably at least about 30%, and more preferably at least about 90% by weight of total nucleic acid present in a given fraction.

Also encompassed by the invention are nucleic acids that are hybridizable to, or derived from, the DRAP sequences described above.

A nucleic acid or polypeptide sequence that is "derived from" a designated sequence refers to a sequence that is related in nucleotide or amino acid sequence to a region of the designated sequence. For nucleic acid sequences, this encompasses sequences that are homologous or complementary to the sequence, as well as "sequence-conservative variants" and "function-conservative variants." For polypeptide sequences, this encompasses "function-conservative variants." Sequence-conservative variants are those in which a change of one or more nucleotides in a given codon position results in no alteration in the amino acid encoded at that position. Function-conservative variants are those in which a given amino acid residue in a polypeptide has been changed without altering the overall conformation and function of the native polypeptide, including, but not limited to, replacement of an amino acid with one having similar physico-chemical properties (such as, for example, acidic, basic, hydrophobic, and the like). "Function-conservative" variants of a designated polypeptide also include any polypeptides that have the ability to elicit antibodies specific to the designated polypeptide.

Nucleic acids are "hybridizable" to each other when at least one strand of nucleic acid can anneal to another nucleic acid strand under defined stringency conditions. Stringency of hybridization is determined, e.g., by a) the temperature at which hybridization and/or washing is performed, and b) the ionic strength and polarity (e.g., formamide concentration) of the hybridization and washing solutions, as well as other parameters. Hybridization requires that the two nucleic acids contain substantially complementary sequences; depending on the stringency of hybridization, however, mismatches may be tolerated. The appropriate stringency for hybridizing nucleic acids depends on the length of the nucleic acids and the degree of complementarity, variables well known in the art.

In one embodiment, the invention relates to isolated nucleic acids capable of hybridizing with the DRAP sequences above or with their complements under high stringency hybridization conditions, an example of which is defined below.

Prehybridization treatment of the support (e.g. nitrocellulose filter or nylon membrane), to which is bound the nucleic acid capable of hybridizing with that of *D. melanogaster* DRAP, at 65° C. for 6 hours with a solution having the following composition: 4×SSC, 10× Denhardt (1× Denhardt is 1% Ficoll, 1% polyvinylpyrrolidone, 1% BSA (bovine serum albumin); 1×SSC consists of 0.15M of NaCl and 0.015M of sodium citrate, pH 7);

Replacement of the pre-hybridization solution in contact with the support by a buffer solution having the following composition: 4×SSC, 1× Denhardt, 25 mM NaPO$_4$, pH 7, 2 mM EDTA, 0.5% SDS, 100 µg/ml of sonicated salmon sperm DNA containing a nucleic acid derived from the sequence of the DRAP as probe, in particular a radioactive probe, and previously denatured by a treatment at 100° C. for 3 minutes;

Incubation for 12 hours at 65° C.;

Successive washings with the following solutions: (i) four washings with 2×SSC, 1× Denhardt, 0.5% SDS for 45 minutes at 65° C.; (ii) two washings with 0.2×SSC, 0.1×SSC for 45 minutes at 65° C.; and (iii) 0.1×SSC, 0.1% SDS for 45 minutes at 65° C.

The invention also encompasses any nucleic acid exhibiting the property of hybridizing specifically with the above-described *D. melanogaster* DRAP under the conditions described above, but at approximately 40° C., including successive washings in 2×SSC at 45° C. for 15 minutes.

It will be understood that the conditions of hybridization defined above constitute preferred conditions for the hybridization, but are in no way limiting and may be modified without in any way affecting the properties of recognition and hybridization of the probes and nucleic acids mentioned above.

The salt conditions and temperature during the hybridization and the washing of the membranes can be modified in the sense of a greater or lesser stringency without the detection of the hybridization being affected. For example, it is possible to add formamide in order to lower the temperature during hybridization.

Nucleic acids that hybridize to the DRAP sequences of the invention may be of any length. In one embodiment, such polynucleotides are at least 8–25, preferably at least 100 and most preferably at least 200 nucleotides long. In another embodiment, the polynucleotide that hybridizes to the polynucleotide of the invention is of the same length as the polynucleotide of the invention.

"Functional homology" to DRAP polypeptide is defined by one or more biochemical properties specific to DRAP that are shared. Examples of such properties include recombinase and topoisomerase activity, and demonstration of antigenicity using anti-DRAP antibodies.

"Non-homogeneous" as used herein is defined as a fraction which is not purified to homogeneity.

DRAP-Encoding Nucleic Acids and Polypeptides

The present invention encompasses nucleic acid sequences from *D. melanogaster* that encode for DRAP as depicted in FIGS. 1A–B, e.g. the nucleotide sequence of an isolated cDNA clone containing the coding region for DRAP [SEQ ID NO: 1], a DNA encoding DRAP corresponding to nt 134–610 of the cDNA clone [SEQ ID NO: 2] and the longest Open Reading Frame (ORF) in the cDNA sequence corresponding to nt 104–610 of the cDNA clone [SEQ ID NO: 3]. Methods used for determining the relevant nucleic acid sequences are described in Example 1 below, and the deduced DRAP amino acid sequence, i.e. the gene encoding the DRAP polypeptide from *D. melanogaster* [SEQ ID NO: 4], of approximately 20 kDa is shown in FIGS. 2A–E and 4B.

The present invention encompasses DNA and RNA sequences, and sense and antisense sequences. DRAP-encoding sequences according to the present invention may be modified by transitions, transversions, deletions, insertions, or other modifications such as alternative splicing. The invention also encompasses genomic DRAP sequences and DRAP gene flanking sequences, including DRAP regulatory sequences. Nucleic acid sequences encoding DRAP polypeptides may also be associated with heterologous sequences, including promoters, enhancers, response elements, signal sequences, polyadenylation sequences, introns, 5'- and 3'-noncoding regions, and the like. Other useful heterologous sequences are known to those skilled in the art. Furthermore, the nucleic acids can be modified to alter stability, solubility, binding affinity and specificity. For example, DRAP encoding sequences can be selectively methylated. The nucleic acid sequences of the present invention may also be modified with a label capable of providing a detectable signal, either directly or indirectly. Exemplary labels include radioisotopes, fluorescent molecules, biotin, and the like.

In general, nucleic acid manipulations according to the present invention use methods that are well known in the art, as disclosed in e.g. *Molecular Cloning, A Laboratory Manual*, 2nd Ed., Sambrook, Fritsch and Maniatis, Cold Spring Harbor; or *Current Protocols in Molecular Biology*, Eds. Ausubel, Brent, Kingston, Moore, Seidman, Smith and Struhl, Greene Publ. Assoc., Wiley-Interscience, NY, N.Y., 1992 and regularly updated versions.

The invention also encompasses any hybridizable nucleic acid exhibiting the property of hybridizing specifically with the above-described DRAP-encoding DNA under the hybridization conditions described above, but at 40° C., including successive washings in 2×SSC at 45° C. for 15 minutes.

It will be understood that the conditions of high stringency hybridization defined above constitute preferred conditions for hybridization, but are in no way limiting and may be modified in ways known in the art which do not affect the overall properties of recognition and hybridization of the probes and nucleic acids mentioned above.

The invention also encompasses vectors comprising DRAP-encoding nucleotide sequences, cells comprising the vectors, and methods for producing DRAP that involve culturing the cells.

A large number of vectors, including plasmid and fungal vectors, have been described for expression in a variety of eukaryotic and prokaryotic hosts. Such vectors will often include one or more replication systems for cloning or expression, one or more markers for selection in the host, e.g. antibiotic resistance, and one or more expression cassettes. The inserted DRAP coding sequences may be synthesized, isolated from natural sources, prepared as hybrids, etc. Ligation of the coding sequences to the transcriptional regulatory sequences may be achieved by known methods. Suitable host cells may be transformed/transfected/infected by any suitable method including electroporation, CaCl$_2$ mediated DNA uptake, fungal infection, microinjection, microprojectile, or other established methods known in the art.

A wide variety of host/expression vector combinations may be employed in expressing DNA sequences encoding DRAP. Useful expression vectors, for example, may consist of segments of chromosomal, non-chromosomal and synthetic DNA sequences. Suitable vectors include derivatives of SV40 and known bacterial plasmids, e.g., *E. coli* plasmids col E1, pCR1, pBR322, pMal-C2, pET, pGEX (Smith et al., Gene 67:31–40, 1988), pMB9 and their derivatives, plasmids such as RP4; phage DNAs, e.g., the numerous derivatives of phage 1, e.g., NM989, and other phage DNA, e.g., M13 and filamentous single stranded phage DNA; yeast plasmids such as the 2 micron plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Appropriate host cells for expressing protein include bacteria, Archaebacteria, fungi, especially yeast, and plant and animal cells, especially mammalian cells. Of particular interest are E. coli, B. subtilis, S. cerevisiae, Sf9 cells, C129 cells, 293 cells, Neurospora, and CHO cells, COS cells, HeLa cells, and immortalized mammalian myeloid and lymphoid cell lines. Preferred replication systems include M13, ColE1, SV40, baculovirus, lambda, adenovirus, and the like. A large number of transcription initiation and termination regulatory regions have been isolated and shown to be effective in the transcription and translation of heterologous proteins in the various hosts. Examples of these regions, methods of isolation, manner of manipulation, etc. are known in the art. Under the appropriate expression conditions, host cells can be used as a source of recombinantly produced DRAP.

Advantageously, vectors may also include a promoter sequence operably linked to the DRAP encoding portion. The encoded DRAP may be expressed by using any suitable vectors and host cells, using methods disclosed or cited herein or otherwise known to those skilled in the relevant art. The particular choice of vector/host is not critical to the invention.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

Expression of DRAP or DRAP fragments may be controlled by any promoter/enhancer element known in the art, but these regulatory elements must be functional in the host selected for expression. Promoters which may be used to control DRAP gene expression include, but are not limited to, Cytomegalovirus ("CMV") immediate early promoter (CMV promoter; U.S. Pat. Nos. 5,385,839 and 5,168,062) the SV40 early promoter region (Benoist and Chambon, 1981, Nature 290: 304–310), the promoter contained in the 3' long terminal repeat of Rous sarcoma virus (Yamamoto, et al., 1980, Cell 22: 787–797), the herpes thymidine kinase promoter (Wagner et al., 1981, Proc. Natl. Acad. Sci. U.S.A. 78: 1441–1445), the regulatory sequences of the metallothionein gene (Brinster et al., 1982, Nature 296: 39–42); prokaryotic expression vectors such as the β-lactamase promoter (Villa-Kamaroff, et al., 1978, Proc. Natl. Acad. Sci. U.S.A. 75: 3727–3731), or the tac promoter (DeBoer, et al., 1983, Proc. Natl. Acad. Sci. U.S.A. 80: 21–25); see also "Useful proteins from recombinant bacteria" in Scientific American, 1980, 242: 74–94; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al., 1984, Cell 38: 639–646; Ornitz et al., 1986, Cold Spring Harbor Symp. Quant. Biol. 50: 399–409; MacDonald, 1987, Hepatology 7: 425–515); insulin gene control region which is active in pancreatic beta cells (Hanahan, 1985, Nature 315: 115–122), immunoglobulin gene control region which is active in lymphoid cells (Grosschedl et al., 1984, Cell 38: 647–658; Adames et al., 1985, Nature 318: 533–538; Alexander et al., 1987, Mol. Cell. Biol. 7: 1436–1444), mouse mammary tumor virus control region which is active in testicular, breast, lymphoid and mast cells (Leder et al., 1986, Cell 45: 485–495), albumin gene control region which is active in liver (Pinkert et al., 1987, Genes and Devel. 1: 268–276), alpha-fetoprotein gene control region which is active in liver (Krumlauf et al., 1985, Mol. Cell. Biol. 5: 1639–1648; Hammer et al., 1987, Science 235:53–58), alpha 1-antitrypsin gene control region which is active in the liver (Kelsey et al., 1987, Genes and Devel. 1: 161–171), beta-globin gene control region which is active in myeloid cells (Mogram et al., 1985, Nature 315: 338–340; Kollias et al., 1986, Cell 46: 89–94), myelin basic protein gene control region which is active in oligodendrocyte cells in the brain (Readhead et al., 1987, Cell 48: 703–712), myosin light chain-2 gene control region which is active in skeletal muscle (Sani, 1985, Nature 314: 283–286), and gonadotropic releasing hormone gene control region which is active in the hypothalamus (Mason et al., 1986, Science 234: 1372–1378).

Nucleic acids encoding wild-type or variant DRAP polypeptides may also be introduced into cells by recombination events. For example, such a sequence can be introduced into a cell, and thereby effect homologous recombination at the site of an endogenous gene or a sequence with substantial identity to the gene. Other recombination-based methods, such as non-homologous recombinations or deletion of endogenous genes by homologous recombination, may also be used.

The invention also encompasses isolated and purified DRAP polypeptides, including, e.g., a polypeptide having the amino acid sequence depicted in FIGS. 2A–E and 4B [SEQ ID NO: 4] as well as function-conservative variants of this polypeptide, including fragments that retain recombinase and/or topoisomerase activity as described above, and antigenic DRAP peptides, examples of which have the amino acid sequence depicted in FIG. 4B [SEQ ID NO: 5], [SEQ ID NO: 6] and [SEQ ID NO: 7].

DRAP-derived polypeptides according to the present invention, including function-conservative variants, may be isolated from wild-type or mutant D. melanogaster cells, or from heterologous organisms or cells (including, but not limited to, bacteria, fungi, insect, plant, and mammalian cells) into which a DRAP-derived protein-coding sequence has been introduced and expressed. Furthermore, the polypeptides may be part of recombinant fusion proteins. Alternatively, polypeptides may be chemically synthesized by commercially available automated procedures, including, without limitation, exclusive solid phase synthesis, partial solid phase methods, fragment condensation or classical solution synthesis.

The DRAP amino acid sequence [SEQ ID NO: 4] possesses a number of potential sites for post-translational modification of the encoded protein as determined by using the Prosite® analysis software program (ExpasY). These post-translational modification sites may be important for biological function of the recombinase and include the following:

1) N-glycosylation site beginning at amino acid number 4 is defined by the amino acid sequence NNSS [SEQ ID NO: 33].

2) cAMP- and cGMP-dependent protein kinase phosphorylation site beginning at amino acid number 137 is defined by the amino acid sequence RKLT [SEQ ID NO: 34].

3) Protein kinase C phosphorylation sites beginning at amino acid numbers 23, 43 and 81 are defined by the amino acid sequences TFK, TRR and SPK, respectively.

4) Casein kinase II phosphorylation site beginning at amino acid number 7 is defined by the amino acid sequence STTD [SEQ ID NO: 35].

5) N-myristylation sites beginning at amino acid numbers 30, 39, 52 and 149 are defined by the amino acid sequences GSEVAR [SEQ ID NO: 16], GIKYTR [SEQ ID NO: 17], GVAKNL [SEQ ID NO: 18] and GLLATG [SEQ ID NO: 19], respectively.

DRAP has no close homologues but shares a short motif identified as MIVVKDESSP [SEQ ID NO: 15] and shown in FIG. 4D, which is related to a motif found in several general recombinases and other recombination-associated proteins (Camerini-Otero, R. D., et al., 1995; and Heyer, W. D., 1994, Experientia 50: 223–233.). DRAP also contains several DDE motifs. (See FIGS. 4B and 4C.) The DDE motif is found in a number of transposases and retroviral integrases. (Bushman, F. D., et al., 1993, Proc. Nat. Acad. Sci. 90: 34283432; Cheng, C., et al., 1998, Cell 92: 841–850; Gangloff, S., et al., 1994, Experientia 50: 261–269; Rice, P. et al., 1995, Cell 82: 209–220; and Sherratt, D. J., et al., 1998, Cell 93: 149–152.) Three amino acids, namely, D, D and E, have been shown to be involved in catalysis and are found in otherwise unrelated proteins. The D, D and E amino acids in the motif are separated by a variable number of amino acids as shown in FIG. 4B.

"Purification" of DRAP refers to the isolation of the polypeptide in a form that allows its recombinase/topoisomerase activity to be measured without interference by other components of the cell in which the polypeptide is expressed. Methods for polypeptide purification are well-known in the art, including, without limitation, preparative disc-gel electrophoresis, isoelectric focusing, HPLC, reversed-phase HPLC, gel filtration, ion exchange and partition chromatography, and countercurrent distribution. For some purposes, it is preferable to produce the polypeptide in a recombinant system in which the protein contains an additional sequence tag that facilitates purification, such as, but not limited to, a polyhistidine ("His$_6$") sequence. The polypeptide can then be purified from a crude lysate of the host cell by chromatography on an appropriate solid-phase matrix. Alternatively, antibodies produced against DRAP or against peptides derived therefrom can be used as purification reagents. Other purification methods known in the art are possible.

Proteins that interact strongly with DRAP can be used in a variety of methods to (affinity) purify DRAP, enhance or inhibit DRAP activity or substitute for immunoaffinity reagents (antibodies) in the detection of DRAP or DRAP homologues. DRAP-interacting proteins can identified by a variety of techniques such as co-immunoprecipitation, co-purification or by genetic techniques such as that utilized in the yeast two-hybrid method (Drees, B. L, Curr Opinions Chem Biol. 3: (1999) 64–70), functional screening of expression libraries with DRAP and variations thereof.

The isolated polypeptides may be modified by, for example, phosphorylation, sulfation, acylation, or other protein modifications. They may also be modified with a label capable of providing a detectable signal, either directly or indirectly, including, but not limited to, radioisotopes and fluorescent compounds.

In a standard strand transfer assay (see FIGS. 3C, 6C and 7; and Examples 1 and 6 below), homologous M13 phage double stranded linear and single stranded circular DNAs were incubated together for various times, deproteinized with SDS and followed by agarose gel electrophoresis. Highly purified, but non-homogeneous, native protein fractions have a potent strand transferase activity (Eisen, et. al., 1988.) and yield bands correlated with joint molecules and/or nicked circles.

Figure 3C:
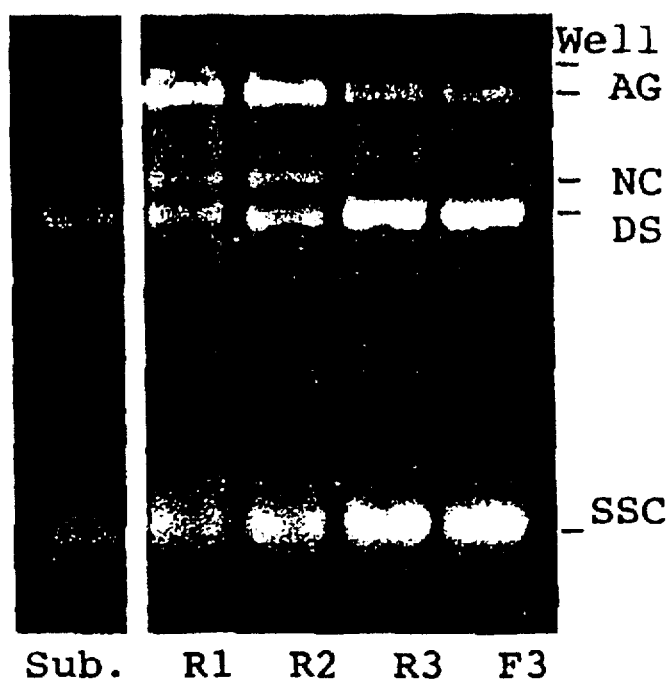
FIG. 3C is a photograph of a 0.8% agarose 1×TAE (Tris Acetate EDTA) gel demonstrating the formation of DNA aggregates (AG), nicked circles (NC) joint molecules from double stranded (DS) and single stranded circular (SSC) DNA by protein fractions retained in each of the purification steps shown in FIG. 3B.
Figure 3D:
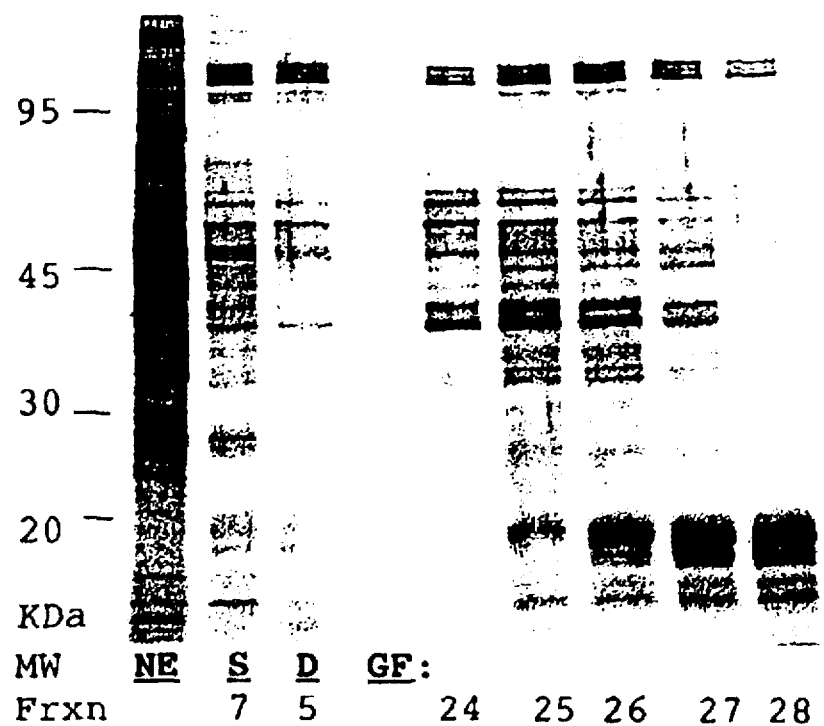
FIG. 3D is a photograph of a silver-stained SDS-PAGE protein gel of the starting nuclear extract (NE) and active fractions eluted from the—Sepharose (S), SS DNA (D) and Sephacryl HR-200 gel filtration (GF) columns.

The non-homogeneous fractions were enriched for a 20 kDa species that was immunoreactive with neutralizing IgM monoclonal antibody when run on a polyacrylamide gel. (FIG. 3D, fraction 28.) Most forms of bacterially expressed recombinant DRAP protein exhibited a weak strand transferase activity when ethidium bromide-stained agarose gels were examined for the appearance of joint molecules or nicked circles.

Initially, the reason for the apparently poor strand transferase activity exhibited by the recombinant protein was not clear. It was determined that the absence of joint molecules and nicked circles was due to the presence of another recombination-related activity exhibited by the recombinant DRAP protein, namely topoisomerase activity.

Topoisomerase activity is an important feature of general homologous recombination utilized to resolve joint molecules formed by strand transferase activity. (Gangloff, S., et al., 1994; Dunderdale, H. J., et al., 1991, Nature 354: 506–510; and Eggleston, A. K., et al., 1997, Cell 89: 607–617.) This activity is not a feature of the known general recombinases of the RecA/Rad51 family or their active peptides. However, as noted above, topoisomerase activity has been shown to be an integral property of the prokaryotic site-specific recombinases, transposases and viral integrases that share the DDE motif. Because DRAP contains several potential DDE motifs, it was examined for topoisomerase activity.

The DRAP recombinant protein, as defined by [SEQ ID NO:4] exhibits a potent, ATP independent, topoisomerase-like activity. Incubation of the protein with a mixed supercoiled/nicked circular substrate lead to the relaxation and subsequent linearization of the substrates (See Example 6 and FIG. 6D). Because nicked circles are the end product of a completed strand transfer reaction in the assay with M13 DNA, it was postulated that these products were further converted by the DRAP protein topoisomerase activity to a new double stranded linear molecule. Thus, in the standard strand transfer assay with M13 viral DNA substrate, the DRAP protein demonstrated both strand transferase and topoisomerase activities. Nicked circular products that formed became linearized and, in this case, the displaced linear single strand migrated similarly to the single strand circle, and made it appear that there was little or no strand transferase activity on ethidium-stained agarose gels. Strand transfer can be shown, however, by end-labeling the duplex substrate (see FIGS. 6E and 6F).

Figure 9:
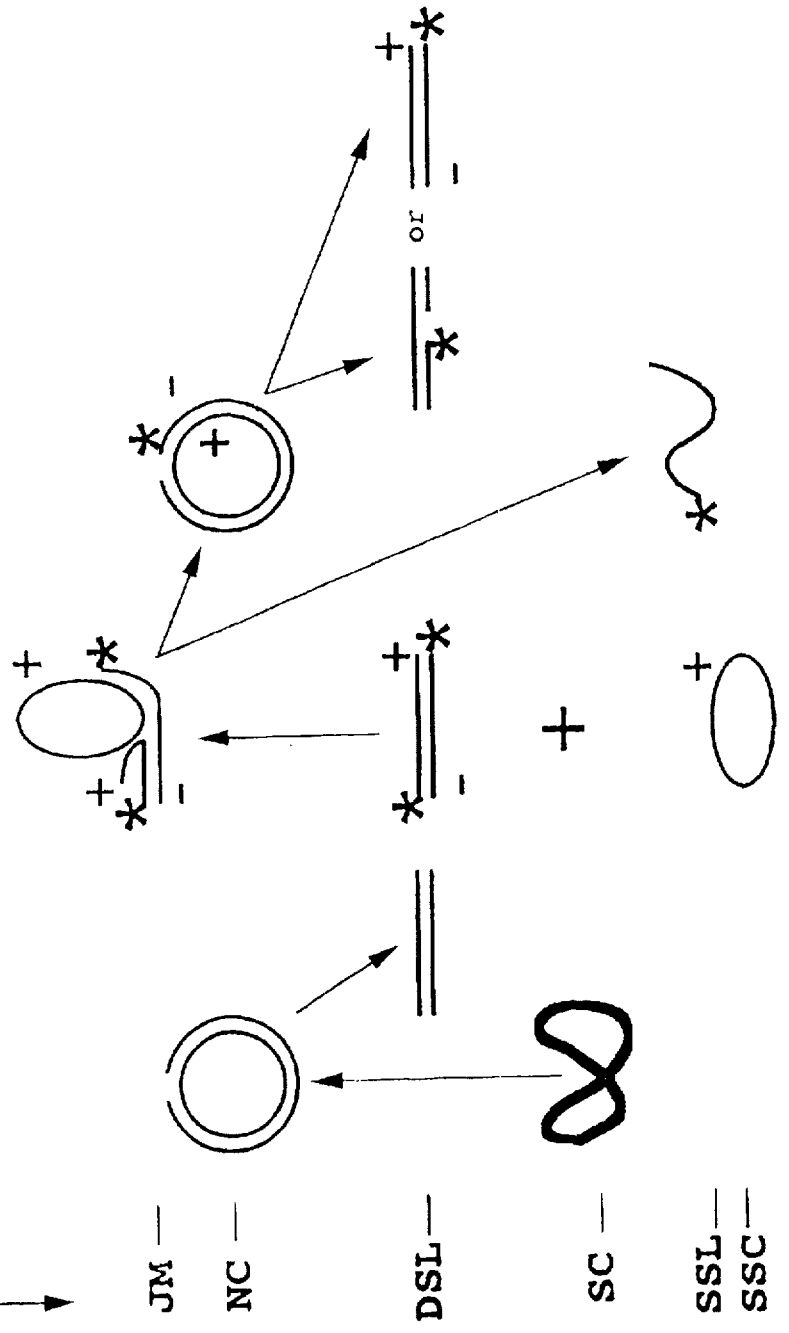
FIG. 9 depicts a model of DRAP driven molecular DNA reactions.

In the end labeling experiment, where both ends of the duplex were end-labeled with $^{32}$P, the fate of both strands of the duplex was observed. In a reaction that required both single strand and double strand DNA as well as ATP and magnesium, one strand was displaced from the duplex substrate by the invading single stranded circular substrate. The nicked circle that forms is converted to a linear duplex identical in length to the starting substrate. The displaced linear single stranded DNA migrated slightly behind the single stranded circular substrate. Complete strand transfer occurred and the nicked circular intermediate product was linearized (FIG. 9). The examples discussed here and provided below demonstrate that DRAP carries out both strand transfer and topoisomerase-activity.

Anti-DRAP Antibodies

The present invention also encompasses antibodies that are specific for DRAP or fragments of DRAP as described above, including, but not limited to, antibodies generated against peptides defined by [SEQ ID NO: 5], SEQ ID NO: 6] and [SEQ ID NO:7]. As used herein, antibodies "specific" for DRAP include, without limitation, antibodies that: bind to DRAP but do not bind to other nuclear proteins bind Rec-A-like proteins with DDE motifs from non-Drosophila species with a lower affinity than to DRAP; identify associational or other functional domains present in DRAP but not in other species, and the like. The antibodies may be polyclonal or monoclonal. The antibodies may be elicited in an animal host by immunization with DRAP or fragments derived therefrom or may be formed by in vitro immunization of immune cells. The immunogens used to elicit the antibodies may be isolated from *D. melanogaster* cells or produced in recombinant systems.

The antibodies may also be produced in recombinant systems programmed with appropriate antibody-encoding DNA. Alternatively, the antibodies may be constructed by biochemical reconstitution of purified heavy and light chains. The antibodies include hybrid antibodies (i.e., containing two sets of heavy chain/light chain combinations, each of which recognizes a different antigen), chimeric antibodies (i.e., in which either the heavy chains, light chains, or both, are fusion proteins), and univalent antibodies (i.e., comprised of a heavy chain/light chain complex bound to the constant region of a second heavy chain). Also included are Fab fragments, including Fab' and F(ab)$_2$ fragments of antibodies.

Methods for the production of all of the above types of antibodies and derivatives are well-known in the art and are discussed in more detail below. For example, techniques for producing and processing polyclonal antisera are disclosed in Mayer and Walker, 1987, *Immunochemical Methods in Cell and Molecular Biology*, (Academic Press, London). Such antibodies are conveniently made using the methods and compositions disclosed in Harlow and Lane, *Antibodies, A Laboratory Manual*, Cold Spring Harbor Laboratory, 1988, as well as immunological and hybridoma technologies known to those of ordinary skill in the art. Where natural or synthetic DRAP-derived peptides are used to induce a DRAP-specific immune response, the peptides may be conveniently coupled to a suitable carrier such as KLH and administered in a suitable adjuvant such as Freunds. Preferably, selected peptides are coupled to a lysine core carrier substantially according to the methods of Tam (Proc. Natl. Acad. Sci. USA 85:5409, 1988).

In one embodiment, purified recombinant DRAP is used to immunize mice, after which their spleens are removed, and splenocytes used to form cell hybrids with myeloma cells and obtain clones of antibody-secreted cells using techniques that are standard in the art. The resulting monoclonal antibodies can be screened using in vitro assays such as those described above for binding to DRAP.

Anti-DRAP antibodies may be used to quantify DRAP, using immunoassays such as, but not limited to ELISA. Anti-DRAP antibodies may also be used to identify, isolate, and purify DRAP or related proteins from different sources, and to perform subcellular and histochemical localization studies.

Potential Applications For DRAP

Overview

Figure 10:
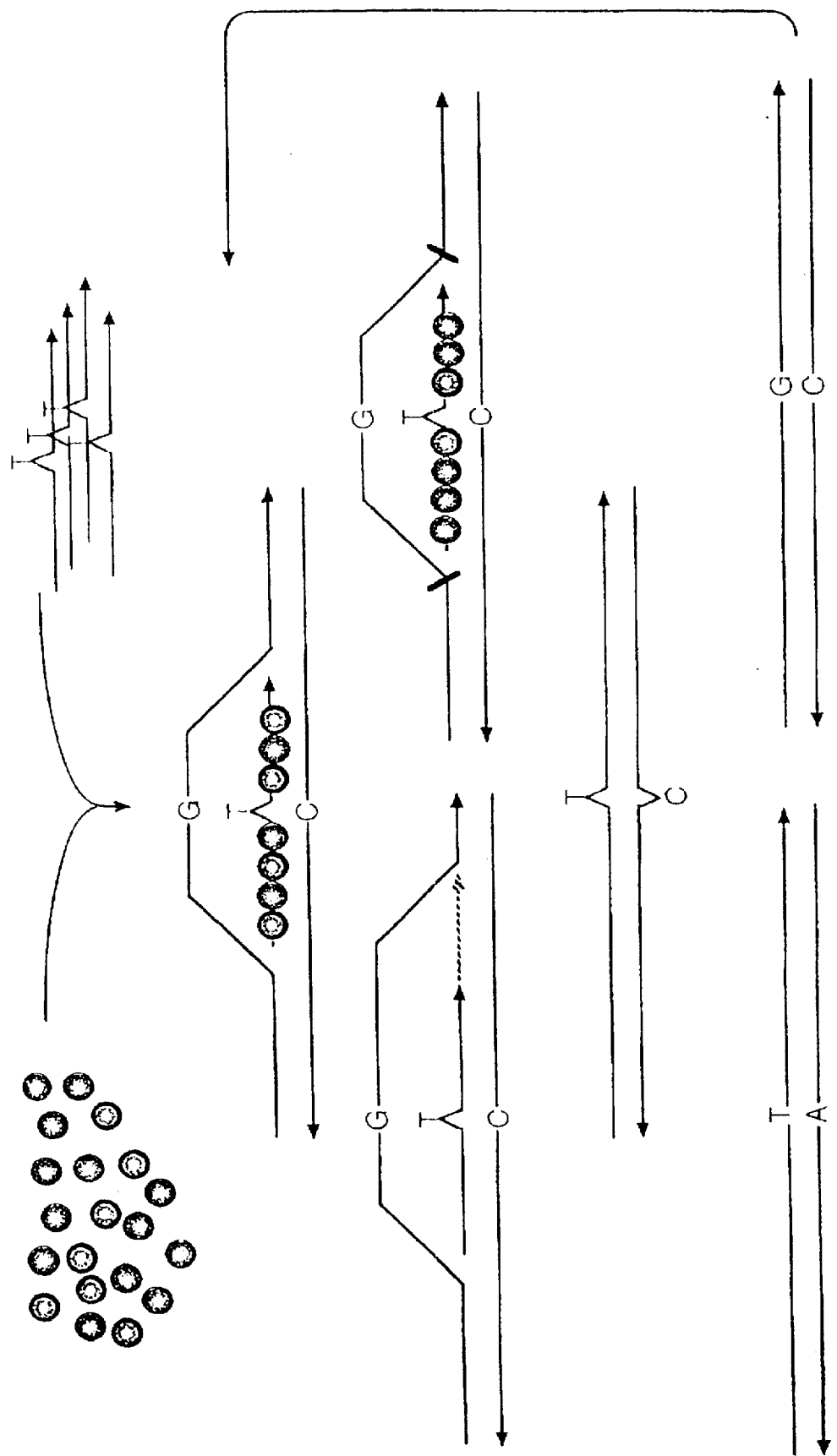
FIG. 10 depicts a diagram of a model for gene conversion driven by a recombinase and an oligonucleotide.

The Drosophila Recombination Associated Protein, its homologues from other organisms or active peptides derived therefrom, are useful in any situation in which homology-dependent pairing of three DNA strands is desired. DRAP may be used to pair a single stranded probe or nucleic acid (RNA, DNA, PNA or other DNA compatible chemically-derived purine/pyrimidine base-pairing oligonucleotide) having a native or mutant sequence to homologous regions in any duplex DNA such as genomic DNA, isolated linear DNA or cloned DNA in vivo or in vitro. In addition to its use with single stranded nucleic acids DRAP may be used with any duplex DNAs and/or duplex RNAs which possess single stranded extensions at either the 5' or 3' ends. Basic methods for carrying out such homology-dependent pairings are as follows: pre-incubation (complexing) of DRAP and the specific single-stranded probe(s) (or double stranded with single stranded ends) followed by (i) addition of the complexed material to a duplex DNA, in vivo or in vitro, and (ii) incubation. Upon incubation, the probe-DRAP mixture would enzymatically modify the duplex DNA. A diagram depicting gene conversion events driven by a recombinase and an oligonucleotide is provided in FIG. 10.

The additions in vivo are carried out according to any art recognized method including but not limited to any one of the commonly used transformation, transfection, electroporation, microinjection, or ballistic methods that use chemical, physical or biological means to introduce DNA and protein into isolated cells or the cells of specific tissues or organs and/or their DNA and RNA-containing compartments and organelles such as the mitochondria and nuclei. (See, *Current Protocols in Molecular Biology* 1992 and regularly updated versions.

The combination of strand-transfer and topoisomerase (cleavage) DRAP activities allows for directed pairing and cleavage at defined site(s) within DNA. This in turn permits the isolation and/or removal of a defined segment of DNA. DRAP could be used alone or in combination with other DNA-modifying enzymes and/or proteins to effect subsequent manipulation of the target duplex DNA.

DRAP can also be used to replace RecA (+/−SSB), RAD 51 (+/−RAD 52) or their homologues and biochemically active peptides in a variety of current methods, e.g. the RARE method. (Ferrin, L. J. et al., 1994; and Ferrin, L. J., 1995.) This would result in an improvement in the efficiency of the reactions involved because DRAP acts catalytically rather than stoichiometrically. In other words, only a single step is involved in the reaction because DRAP contains both strand transferase and topoisomerase activity. (See Example 6 below.)

DRAP can also be modified, at sites that do not diminish its biochemical activities utilizing strand transfer or topoisomerase assays, to include peptide sequences that would direct and/or enhance the delivery of the protein to specific organs or cellular compartments and organelles. One non-limiting example of a system to be used in such directed delivery would include liposomes with organ specific uptake ligands incorporated on them with DRAP and mutagenic DNA encapsulated inside such liposomes. Likewise, the native sequence could be modified by random or directed mutagenesis, resulting in amino acid substitutions, that could be screened and selected for enhancement in the desired biochemical activities of the mutant proteins.

Some of the specific applications for DRAP are noted below.

Cloning

DRAP can act as a "universal" restriction enzyme. A single defined oligonucleotide or pair of oligonucleotides is used to make a defined, single-step cleavage or cleavages in a template duplex DNA. As used herein the term "universal" refers to the ability of DRAP to direct cleavage to any user-specified sequence, the sequence to be cleaved being determined by the homology of the single-stranded (or double stranded with single stranded ends) probe selected to be paired with the duplex DNA to be cleaved in the presence of DRAP. As used herein the term "template duplex DNA" is defined as any double stranded DNA in a genome, plasmid, linear fragment or the like. A pair of such single-step cleavages would lead to a deletion of a defined fragment from the duplex DNA template. Pairing, initiated by defined oligonucleotide sequence(s) and DRAP protein would determine the user-defined cleavage site(s). Examples of such duplex DNA are genomic DNA, isolated linear fragments or DNA contained within any variety of cloning vehicles such as HACs (human artificial chromosomes), YACs (yeast artificial chromosomes), BACs (bacterial artificial chromosomes) and PACs (phage artificial chromosomes), cosmids, plasmids, phagemids, viruses or other vectors.

One method for carrying out such single-step cleavage(s) reaction includes but is not limited to incubation of a defined oligonucleotide(s), DRAP and duplex DNA in a buffer containing NaCl, $Mg^{++}$ and other components optimized for pairing and cleavage at a temperature and pH suitable for the target duplex DNA as is well known in the art and as is described in the Examples below for either the strand transferase or topoisomerase activity assays. As shown below, the reactions initiated by DRAP lead to the homologous recombination of a gene. Such recombination leads to the cutting out of the native DNA. Small oligonucleotides homologous to the gene of interest would lead to the removal of other pieces of the native genomic DNA. The cut DNA fragment or fragments could then be isolated and subjected to further art recognized manipulations in order to clone the desired DNA fragment.

Genomic Cloning & Mapping

The isolation of a defined duplex DNA fragment by sequence-directed cleavage would provide for the cloning of a large gene or gene fragment from genomic DNA when only the complete or partial cDNA sequence is known. Oligonucleotides from the 5' and 3' portion of the known cDNA sequence along with DRAP would be used to cut out a large gene fragment from genomic DNA. The gene fragment could be isolated from the larger high molecular weight genomic DNA by pulse-field gel electrophoresis or other methods. This large genomic fragment could then be used as a high quality probe for genomic library screening or in situ mapping techniques. The ability to make defined cleavages and deletions in duplex DNA, even within the complexity of a whole genome, serves as the basis for genetic modifications of living cells and organisms with DRAP.

DRAP—Promoted Gene Disruption or "Knockout" and Targeted Mutagenesis

DRAP-promoted gene disruption can be carried out in order to generate knock out mutations and to evaluate the effects of such knock outs on the cell and/or animal in which they are generated. It is also possible to evaluate the effect of compounds or disease-related genes in "knockout" animals or cells, e.g., to identify a compound that can compensate for a defect in disrupted gene activity or to determine the effect a particularly knockout has on progression and/or occurrence of disease. This technology permits manipulation of single units of genetic information in their natural position in a cellular genome and to examine the results of that manipulation in the background of a terminally differentiated organism.

A "knockout mammal" is a mammal (e.g., mouse, cat, dog, cow, sheep, goat, etc.) that contains within its genome a specific gene that has been inactivated by the method of gene targeting (see, e.g., U.S. Pat. No. 5,777,195 and U.S. Pat. No. 5,616,491). A knockout mammal includes both a heterozygous knockout (i.e., one defective allele and one wild-type allele) and a homozygous mutant (i.e., two defective alleles). Preparation of a knockout mammal requires first introducing a nucleic acid construct that will be used to suppress or disrupt expression of a particular gene into an undifferentiated cell type termed an embryonic stem cell. This cell is then injected into a mammalian embryo. A mammalian embryo with an integrated cell is then implanted into a foster mother for the duration of gestation. Zhou, et al. (Genes and Development, 9:2623–34, 1995) describes PPCA knock-out mice.

The term "knockout" refers to partial or complete suppression of the expression of at least a portion of a protein encoded by an endogenous DNA sequence in a cell. The term "knockout construct" refers to a nucleic acid sequence that is designed to decrease or suppress expression of a protein encoded by endogenous DNA sequences in a cell. The nucleic acid sequence used as the knockout construct is typically comprised of (1) DNA from some portion of the gene (exon sequence, intron sequence, and/or promoter sequence) to be suppressed and (2) a marker sequence used to detect the presence of the knockout construct in the cell. When the suppression or knockout of a given gene will result in a known and visible phenotype, a marker gene is not required.

Typically, the knockout construct is inserted into a cell, and integrates with the genomic DNA of the cell in such a position so as to prevent or interrupt transcription of the native DNA sequence. Such insertion usually occurs by homologous recombination (i.e., regions of the knockout construct that are homologous to endogenous DNA sequences hybridize to each other when the knockout construct is inserted into the cell and recombine so that the knockout construct is incorporated into the corresponding position of the endogenous DNA). The knockout construct nucleic acid sequence may comprise 1) a full or partial sequence of one or more exons and/or introns of the gene to be suppressed, 2) a full or partial promoter sequence of the gene to be suppressed, or 3) combinations thereof. Typically, the knockout construct is inserted into an embryonic stem cell (ES cell) and is integrated into the ES cell genomic DNA, usually by the process of homologous recombination. This ES cell is then injected into, and integrates with, the developing embryo.

The phrases "disruption of the gene" and "gene disruption" refer to insertion of a nucleic acid sequence into one region of the native DNA sequence (usually one or more exons) and/or the promoter region of a gene so as to decrease or prevent expression of that gene in the cell as compared to the wild-type or naturally occurring sequence of the gene. When this nucleic acid construct is then transfected into a cell, the construct will integrate into the genomic DNA. Thus, many progeny of the cell will no longer express the gene at least in some cells, or will express it at a decreased level, as the DNA is now disrupted by the construct DNA. In addition, constructs with mutations which result in a change in the coding or non-coding portion of the gene that produces a non-functioning gene product could also be used.

Examples of such constructs include, but are not limited to, those constructs containing deletions, inversions, transitions, transversions and alterations in splice donor/acceptor sites.

Previously, homologous recombination carried out in the generation of knockout mutations required the DNA knock out construct to be at least about 1 kilobase (kb) in length and preferably 3–4 kb in length, thereby providing sufficient complementary sequence for recombination upon introduction of the knockout construct into the genomic DNA of the cell. DRAP can facilitate such homologous recombination driven manipulations with large constructs. However, in contrast to the currently practiced methods encompassing complicated and lengthy procedures to establish and generate knockout mice, DRAP provides for the ability to insert into or modify genomic DNA directly in vivo using "oligonucleotides", i.e. less than about 100 bp, by less cumbersome transfection methods. DRAP thus increases the efficiency of the production of transgenic animals.

A mammal in which a gene has been homologously recombined in the manner described above is hereby defined as a transgenic mammal.

The DRAP protein of the invention thus provides for the targeting of a specific mutagenic oligonucleotide or oligonucloctides to one or more cognate gene or genes in a complex genome. As used herein a "mutagenic oligonucleotide" means a DNA sequence that contains a mutation of change within the corresponding endogenous gene sequence. Non-limiting examples of oligonucleotides to be used include those with one or more base substitutions, deletions or insertions in such cognate gene, intron, exon or regulatory element.

The DRAP protein, in conjunction with endogenous DNA repair and recombination proteins known to those skilled in the art, effects a direct modification of the targeted locus. Direct co-injection of protein with mutagenic oligonucleotides into the pronucleus of fertilized mouse eggs results in viable transgenic mammals.

As shown in Examples 7 and 8 below, recombinant DRAP was coinjected with several mutagenic oligonucleotides to induce gene conversion events in transgenic mice producing targeted mutations in the genome of such mice. Microinjected DRAP and a mutagenic oligonucleotide target a specific gene in the genome of a mouse zygote and modify the locus so that the gene's function is ablated (knocked-out). The protocol may use a single oligonucleotide to initiate a single cleavage. That cleavage is then repaired/modified by the double strand DNA break repair enzymes of the cell. When the function of the encoded gene is disturbed by this cleavage/repair process the gene is knocked-out with a frequency of up to about 30%. This direct knock-out approach is considerably easier and less expensive to perform than the methods currently in practice. This method could be further enhanced by the use of two mutagenic oligonucleotides from the gene of interest, as was suggested above for the creation of a deletion to be used in cloning and gene mapping applications. This would produce an interstitial deletion in the gene that is more difficult for a cell to repair than a single double strand break and would thus further enhance the likelihood of ablating gene function.

These methods are generally applicable to all cell types and are not limited to the generation of transgenic animals. One or more native or mutant oligonucleotides and DRAP can also be introduced into a particular cell or organ by any of the known methods described above and known to those skilled in the art. Such an insertion leads to a knockout in a specific cell or organ type and would be useful to ablate function of a disease-causing gene and/or fusion gene in the treatment of metabolic disorders or cancerous states.

DRAP cDNA could also be introduced, first or later, with the specific oligonucleotide, as an episomal genetic element or as a transgene under the control of an appropriately designed expression system that would allow for tissue specific and/or induction agent controlled expression. Such tissue specificity could be achieved via controlled expression of DRAP using a tissue-specific promoter or an inducible promoter. This method also permits targeted modification of specific DNA sequences within genomic DNA of integrated viruses such as, but not limited to, HIV; yeasts; prokaryotes; eukaryotic cells in culture; and cells in organs ex vivo or in vivo. Each of such methods could also be carried out with more than one oligonucleotide as described above.

An example of such a method utilizing HIV DNA would involve the introduction of DRAP protein or an episomal construct containing DRAP cDNA with modified HIV virus oligonucleotides or cDNAs. The exogenous or expressed DRAP would cut the genome-integrated HIV virus as directed by the mutated HIV oligonucleotides or cDNAs at the site of genomic integration, yielding an inactive HIV virus. This method could be used to inactivate any integrated gene or genes with known sequence.

Included within the scope of this invention is a mammalian cell or organ in which two or more genes have been knocked out. Such mammalian cells or organs are generated by repeating the procedures set forth herein for the generation of single knockouts, by introducing an additional oligonucleotide construct, or by breeding mammals, each with a single gene knocked out, to each other, and screening for those with the a double knockout genotype.

RNA Interference

The DRAP associated homology-dependent strand pairing and strand cleavage activities may promote heritable or non-heritable (transient) changes in gene expression by effectively attenuating, knocking out and/or knocking down levels of mRNA expressed from targeted genes through the phenomenon of RNA interference. RNA interference (RNAi) has been referred to in the literature (See Bosher, J. M. et al, Nat Cell Biol, 2000, 2(2): E31–36; and Hunter, C. P., Curr Biol, 1999, 17; 9(12): R440–2) and is also known as gene silencing. RNAi has applications in animal, plant and yeast cells. It is known to involve various genes and gene products but the complete set of genes and gene products involved is unknown. DRAP has the requisite activities to promote such an activity alone and/or in conjunction with endogenous cellular proteins.

Therapeutic Applications

The ability to direct DRAP and oligonucleotide probes to specific cell-types and target specific genes for disruption suggests certain therapeutic uses for this methodology. Certain pathologic conditions are known to result from the expression of mutant endogenous genes (p53, BRCA1, estrogen receptor "ER", et al.) or from expression of integrated viral genes (HIV-1, HIV-2, et al.). Similarly, upregulation of normal genes (e.g., drug transporters) may limit the effectiveness of conventional therapies. When DRAP and targeting probes are introduced by any of the methods described herein into affected cells, then the expression of the disease-causing or disease-promoting genes can be disrupted/ablated. This disruption/ablation can lead to the disorder being cured, ameliorated, or rendered susceptible to conventional therapies.

The use of DRAP and single-stranded (or double stranded with single stranded ends) probes to direct cleavages within endogenous genes that are then repaired by the cell, suggests the use of the methods described herein to be used in genetic therapy. A duplex DNA fragment, with a normal (wild-type) or mutant sequence embedded in the middle, that is flanked by specific single-stranded tails is directed to a specific locus within the genome containing sequences homologous to the single-stranded flanking sequence. DRAP-directed cleavages at each end of the fragment would permit the cell to repair the damage to the endogenous locus by replacement of the endogenous segment with the exogenous fragment. In this manner a simple cassette exchange is effected and the genotype of the cell modified.

EXAMPLES

Example 1
Isolation and Initial Characterization of the *D. melanogaster* Recombination Associated Protein (DRAP) Gene Drosophila embryonic nuclear extracts were fractionated by ammonium sulfate precipitation followed by column chromatography on S-Sepharose, SS-DNA agarose and gel filtration to isolate protein fractions with potent strand transferase activity. FIG. 3A provides a schematic representation of the purification method used. FIG. 3B shows the purification of fractions by elution from a single stranded (SS) DNA agarose column. The fractions were eluted from the SS DNA agarose column in a buffer containing 500 mM NaCl. Protein fractions were serially concentrated on Centricon® centrifugal devices with nominal MW cutoff (NMWCO) filters of 100, 30 and 10 KDa. The material retained (R in FIGS. 3B and 3C) and filtered (F in FIGS. 3B and 3C) by each device was assayed for strand transferase activity with M13 mp18 linearized double stranded DNA (DS) and M13 mp18 single stranded circular DNA (SSC) (FIG. 3C). FIG. 3C demonstrates that activity was present in the tested fractions because high molecular weight protein-DNA aggregates (AG) formed in addition to joint molecules and nicked circles. In the high salt fraction (500 mM NaCl) the active material behaved as if it were >30 KDa. The high salt elution provides for the formation of multimeric DRAP complexes.

FIG. 3D provides a silver-stained protein gel of the starting nuclear extract (NE) and active fractions eluted from the Sepharose (S), SS DNA (D) and Sephacryl HR-200 gel filtration (GF) columns. The activity co-enriched with a 20 KDa species at physiological salt (1×PBS) during gel filtration.

Generating Antibodies to DRAP and Use of Anti-DRAP Antibodies

Highly purified fractions which retained DRAP specific activity, namely the ability to form joint molecules and high molecular weight protein-DNA aggregates, were used to generate polyclonal antisera in rabbits and monoclonal antibodies (IgM) by an in vitro method. (Reading, C. L., 1986, Methods Enzymol. 121: 18–27.) The IgM monoclonal antibodies were isolated by gel filtration from cell culture supernatants and selected for their ability to inhibit strand transfer activity. These antibody preparations proved useful for several purposes.

The IgM monoclonal antibody preparations, while more difficult to use due to their lower affinity as compared to IgG preparations, were used to identify a putative recombinase protein band on Western blots (FIGS. 3E and 3F) and to identify immunoreactive recombinase expression clones as summarized below. IgM antibodies generally have lower affinity than IgG antibodies but were of benefit here because of their monoclonal nature and because their lower affinity allowed for immunopurification of protein under native conditions.

Figures 3E, 3F:
FIG. 3E depicts a Western blot of the purification fraction from the Sephacryl HR-200 gel filtration column described in FIG. 3D and reacted separately with either a rabbit polyclonal antibody (PAb) and a neutralizing mouse monoclonal IgM (Mab).
FIG. 3F depicts a silver stained 10% polyacrylamide gel of fractions eluted from an IgM immunoaffinity column loaded with Drosophila nuclear extract.

First, the antibodies were used to identify active component(s) on Western blots (FIG. 3E). FIG. 3E shows a Western blot of from the Sephacryl HR-200 gel filtration column purification extracts reacted with both a rabbit polyclonal antibody (PAb) and a neutralizing mouse monoclonal IgM (Mab). The data show that a 20 KDa species was immunoreactive with the antibodies.

Second, the antibodies were used in the direct immunoaffinity purification of the active component(s) from Drosophila nuclear extracts (FIG. 3F). FIG. 3F depicts a Western blot demonstrating that a 20 KDa species was isolated directly from nuclear extracts on an IgM immunoaffinity column with small amounts of some other cross-reactive and/or interacting material.

Third, the antibodies were used to screen a Drosophila cDNA expression library in order to identify clones expressing immunoreactive peptide.

Fourth, the antibodies were used to look for immuno-crossreactivity with a number of known recombination-related proteins.

Isolation of Expression Clones and cDNA

Clones that were immunoreactive with two independent antibody preparations were plaque purified. The clone inserts were amplified by PCR and used for Southern blotting with a test oligonucleotide constructed from an amino acid sequence obtained from the presumptive immunoreactive recombinase protein band on a PVDF membrane.

One strongly immunoreactive clone was sequenced and the encoded protein denoted as the Drosophila recombination-associated protein (DRAP). The cDNA clone is 1378 bp in length [SEQ ID NO: 1] and the longest ORF is identified by [SEQ ID NO: 3] and codes for 169 amino acids [SEQ ID NO: 5], although the probable start codon is the Met at codon 11. The DRAP amino acid sequence defined by codons 11–169 is identified as [SEQ ID NO: 4] and is encoded by the DNA nucleotide sequence identified as [SEQ ID NO: 2].

Example 2
DRAP Homology to Other Proteins

There are no significant homologues of the isolated DRAP cDNA or coding sequence as determined through BLAST data base searches. Nevertheless, using the full length Drosophila cDNA as a probe, there is cross hybridization on genomic Southern blots with human DNA. Furthermore, although the BLAST searches found no close amino acid sequence homology and thus no close protein homologues, the reaction with the anti-DRAP antibodies indicated that there was a weak relationship to *E. coli* RecA and a somewhat stronger relationship to both T4 Gene32 protein (a helicase) and (Bovine) Topoisomerase I.

The amino acid sequences predicted to be the most hydrophilic portions of the DRAP protein were identified. These presumptive antigenic sites were used to identify similar amino acid sequences in the immunologically cross-reactive proteins and to search the data bases. In this fashion a 10 amino acid motif [SEQ ID NO: 15] was identified that is most conserved in the Flp site-specific recombinase (FIG. 4D).

Example 3
Localization of the DRAP Gene and Transcript

Polytene chromosome in situ hybridization studies using a digoxigenin labeled DRAP cDNA as a probe showed that the gene for this protein mapped to Drosophila chromosome band 63 C/D. This locus is where the recombination-defective mutation (meiS282) maps genetically.

Figure 5A:
FIG. 5A depicts in situ hybridization studies on embryonic Drosophila nurse cells using a digoxigenin-containing antisense DNA single stranded probe prepared from the DRAP cDNA clone. Bar equals 20 microns.

FIG. 5A depicts in situ hybridization studies on nurse cells in Drosophila embryos using a digoxigenin-containing antisense DNA single stranded probe prepared from the DRAP cDNA clone. Detection of the probe (purple staining) indicated that a maternally-encoded DRAP gene is transcribed in nurse cells of the ovary.

Figure 5B:
FIG. 5B depicts in situ hybridization studies on Drosophila embryos using a digoxigenin-containing antisense DNA single stranded probe prepared from the DRAP cDNA clone. Bar equals 20 microns.

FIG. 5B depicts in situ hybridization studies on Drosophila embryos using the same digoxigenin-containing antisense DNA single stranded DRAP probe. The data indicate that, following maternal expression of DRAP, the transcripts subsequently become uniformly distributed in the embryo. This suggests that the gene product may be involved in mitotic recombination, DNA repair processes and/or germ line development.

Example 4
DRAP Expression

Recombinant forms of the DRAP protein were expressed in vivo from either the Met at the 11th or 60th codon in the ORF of the cDNA with either an N-terminal or a C-terminal (His$_6$) purification epitope. The recombinant proteins expressed in bacteria were purified and examined for DNA strand transferase activity. The recombinant Drosophila recombination-associated protein (DRAP) was expressed from a modified pRSET(B) vector in E coli strain HSM174 (DE3) and contains 11 additional amino acids (incorporating the (His$_6$) purification epitope) at the N-terminus of the open reading frame of the cDNA clone starting at the first Met (codon 11). Expression yielded a protein of approximately 21 kDa.

Recombinant proteins were poorly expressed in and difficult to purify from the insect cell/baculovirus system.

Example 5
Protein Purification
DRAP

Figures 6A, 11:
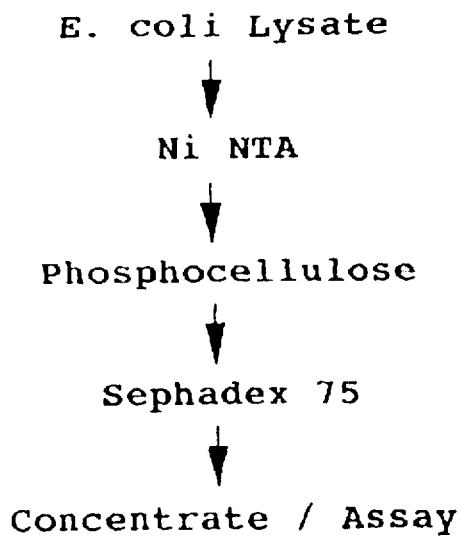
FIG. 6A depicts the scheme for purification of N-terminal, His$_6$-tagged recombinant DRAP successively purified over Ni-NTA (Qiagen), phosphocellulose (Whatman) and Sephadex 75 (Pharmacia) columns followed by centrifugal concentration (Millipore).
FIG. 11 depicts the results of preliminary studies performed with 5'OH-containing oligonucleotides.

A schematic depiction of recombinant protein purification is provided in FIG. 6A. Protein expression in E. coli was induced in a 500 ml Terrific Broth "TB" [10 grams bacto-tryptone, 5 grams bacto-yeast extract and 10 grams NaCl per liter, adjusted to pH 7.0] culture grown to OD$_{600-0.7}$ by IPTG addition to 1 mM for 3 hours. The pelleted bacteria were frozen at −80° C. Subsequently the pellet was resuspended in Basic Buffer "BB" [300 mM NaCl, 50 mM NaPi, pH=8.0] with 0.1% Tween 20 and lysed in a French Press. Insoluble material in the lysate was pelleted by centrifugation. The supernatant was filtered (0.2 μM) and passed over a 5 ml Ni-NTA column (Qiagen). The column was washed in 10 column volumes, each, of BB buffer with 0, 5 and 10 mM imidazole and the recombinant protein eluted with 3 column volumes of BB+250 mM imidazole. The eluted material was concentrated (Millipore Ultrafree 10 KDa device) desalted (Bio Rad 10DG column) into 50 mM NaCl-containing column buffer [x mM NaCl, 15 mM Tris-HCl, 3 mM Mg Acetate, 1 mM EDTA, 0.4 mM PMSF, 10% glycerol, pH=7.5] and put over a 5 ml phosphocellulose column. Weakly adherent proteins were washed away with up to 500 mM NaCl-containing column buffer and the recombinant protein was eluted with 1 M NaCl-containing column buffer. Fractions containing the recombinant protein were pooled, concentrated as before and loaded onto a 250 ml Sehpadex G 75 gel filtration column equilibrated with Transgenic Buffer ("TG") [10 mM NaCl, 10 mM Tris-HCl, 1 mM MgCl$_2$ and 0.1 mM EDTA, pH=7.5]. Individual fractions containing the recombinant protein were concentrated and examined by SDS-PAGE. (See FIG. 6B.) Homogeneous fractions were pooled and filtered (0.2 μM). Protein concentration was determined by the Bradford method (Bio-Rad) with BSA as the standard. The final concentration of the pooled homogeneous material was 60 ng/μl.

E. coli RecA and Single Stranded Binding Proteins

Figure 6B:
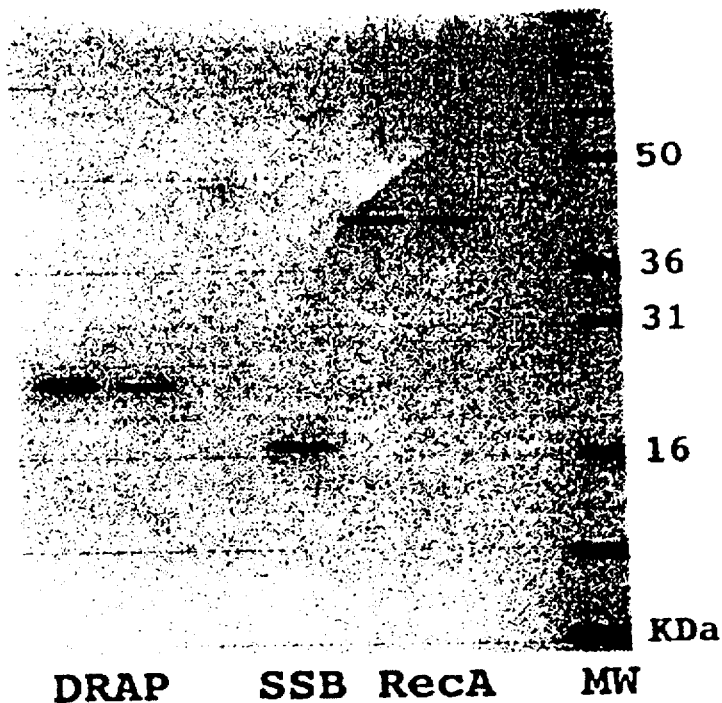
FIG. 6B depicts a 12% polyacrylamide gel electrophoresis of purified DRAP and commercial SSB and RecA proteins (adjusted to 60 ng/µl) seen through Coomassie blue-staining

Homogeneous E. coli RecA protein (Promega) was diluted 1:1 with TG buffer and then desalted over several micro Bio-spin P6 columns (Bio Rad) equilibrated in TG buffer. The final concentration was 480 ng/μl and the material was diluted appropriately for use with TG buffer. FIG. 6B shows both proteins and prestained MW markers (Benchmark, BRIL) after SDS-PAGE on a 12% minigel stained with Coomassie Blue. SSB was similarly prepared in TG buffer.

Example 6
Activity of DRAP

As described above, N-terminal, His$_6$-tagged recombinant DRAP was purified successively over Ni-NTA (Qiagen), phosphocellulose (Whatman) and Sephadex 75 (Pharmacia) columns followed by centrifugal concentration (Millipore). This material was compared with commercial E. coli single strand binding protein (SSB, Promega) and RecA (Promega, Pharmacia and USB) in various assays.

The purified and commercial proteins (adjusted to 60 ng/μl) were seen on a Coomassie blue-stained 12% polyacrylamide gel: DRAP protein (5 and 2.5 μl), SSB (5 μl), and RecA (5 μl; Pharmacia and USB). (FIG. 6B.)

A. DRAP Produces Fewer Joint Molecules Than RecA/SSB

The strand transfer assay described in Example 1 and in FIG. 3C above indicates that DRAP produced fewer joint molecules than RecA/SSB.

Figure 6C:
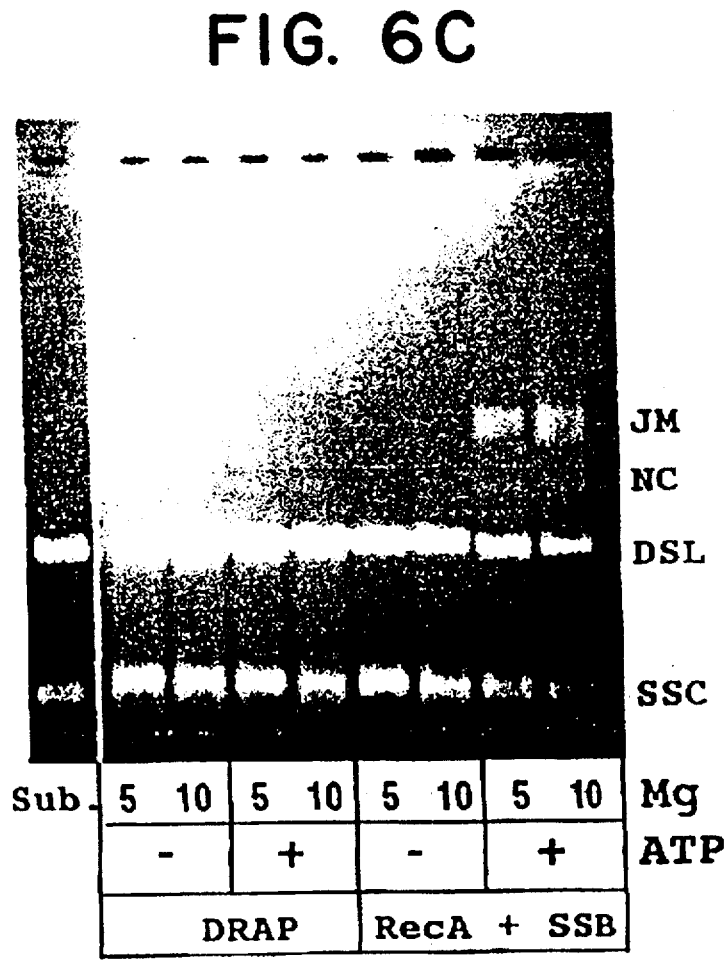
FIG. 6C depicts a 0.8% 1×TAE agarose gel electrophoretic separation of DNA species from a standard strand transfer assay for the production of joint molecules (JM) and nicked circles (NC) produced from double stranded linears (DSL) and single stranded circles (SSC) comparing RecA/SSB (Promega) to DRAP.

In a second standard strand transfer assay RecA/SSB (Promega) appeared to be more efficient than DRAP in producing joint molecules (JM) and nicked circles (NC) from double stranded linears (DSL) and single strand circles (SSC) than DRAP. (FIG. 6C.)

Figure 6D:
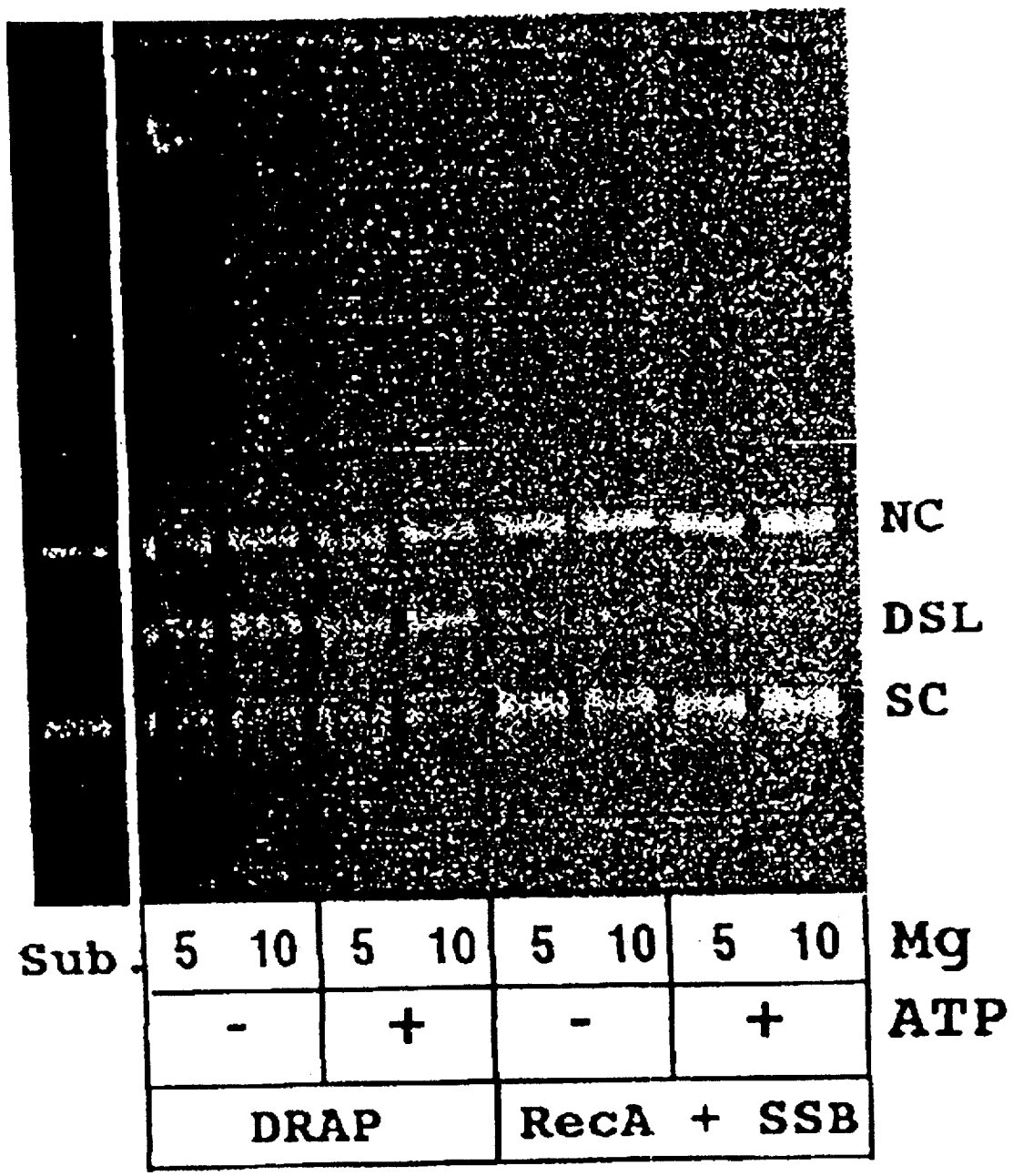
FIG. 6D depicts a 0.8% agarose 1×TAE gel electrophoresis of DNA species resulting from a topoisomerase assay utilizing a plasmid preparation containing both supercoiled (SC) and nicked circular (NC) forms incubated with DRAP (60 ng) or RecA/SSB (240/200 ng) at 37° C. for 30 min.
Figure 6E:
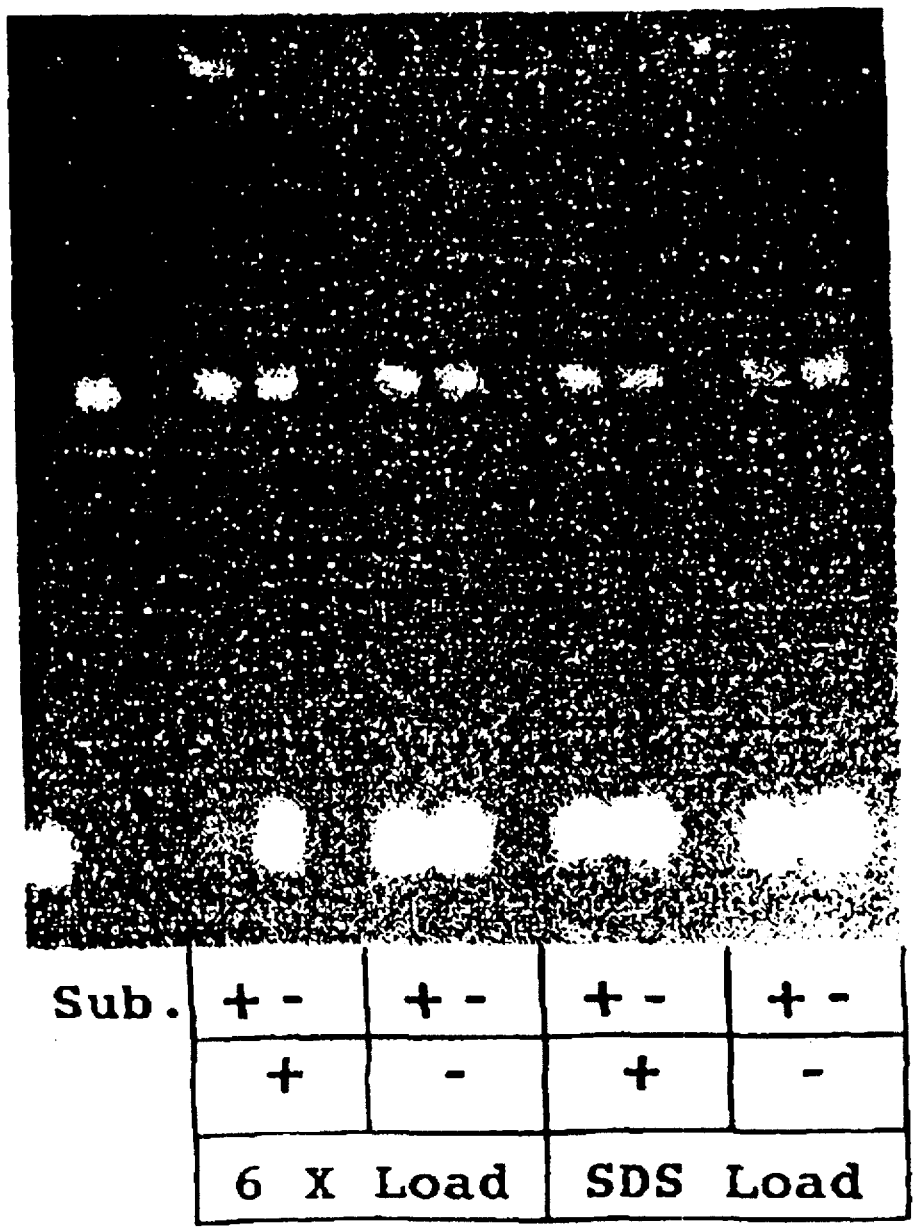
FIG. 6E depicts a 0.8% agarose 1×TAE gel electrophoresis demonstrating that the recombinant DRAP will form large protein-DNA aggregates (AG) with SSC and DSL substrates in a strand transferase assay.

The recombinant DRAP formed large protein-DNA aggregates (AG) with SSC and DSL substrates in a strand transferase assay in the presence of ATP (1 mM) and Mg (10M) but did not yield JMs or NCs after deproteinization with SDS. (FIG. 6E.)

Figure 6F:
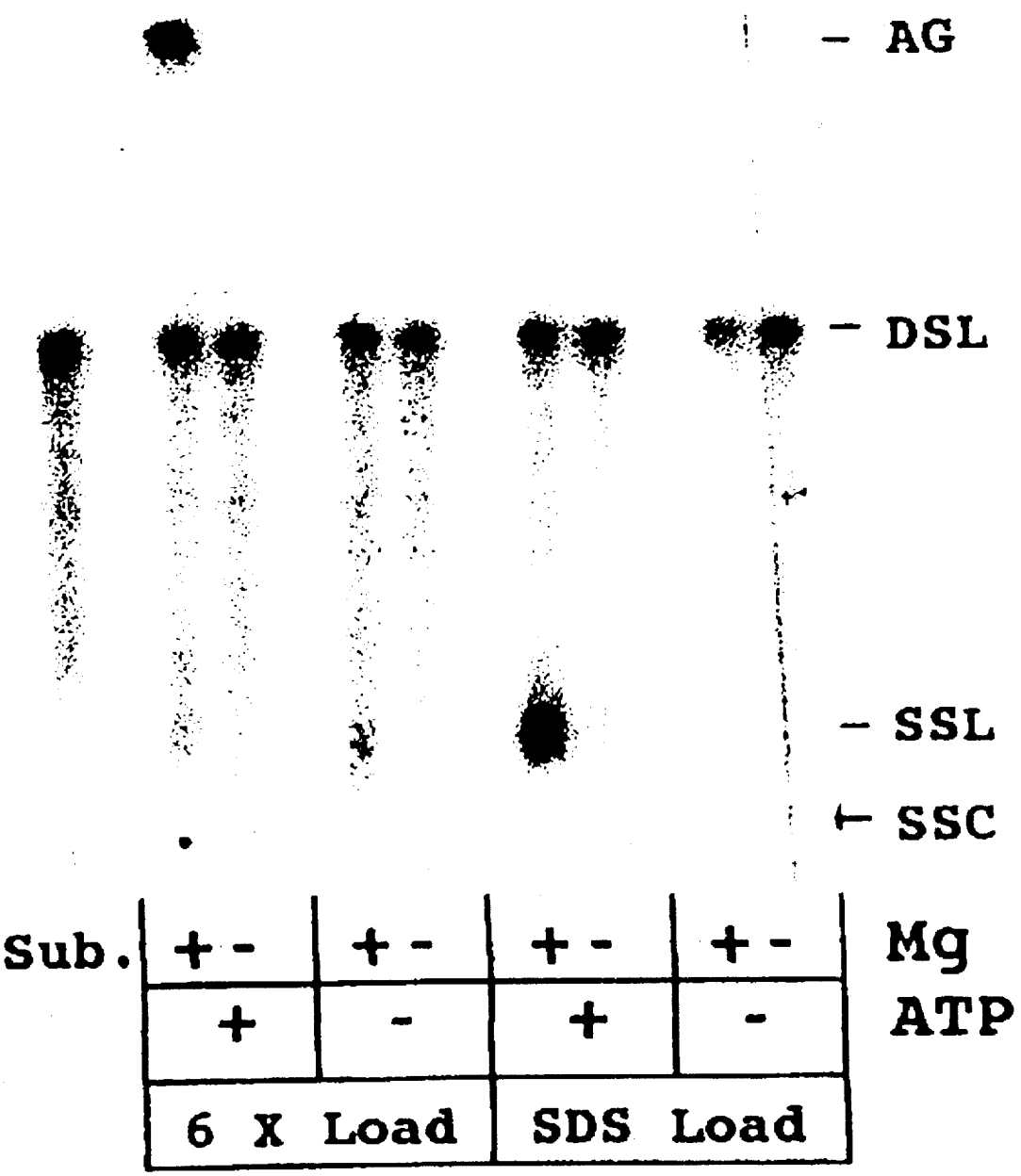
FIG. 6F depicts a 0.8% 1×TAE gel electrophoresis of DNA species produced from a recombinase reaction using an end labeled DSL substrate.
Figure 7:
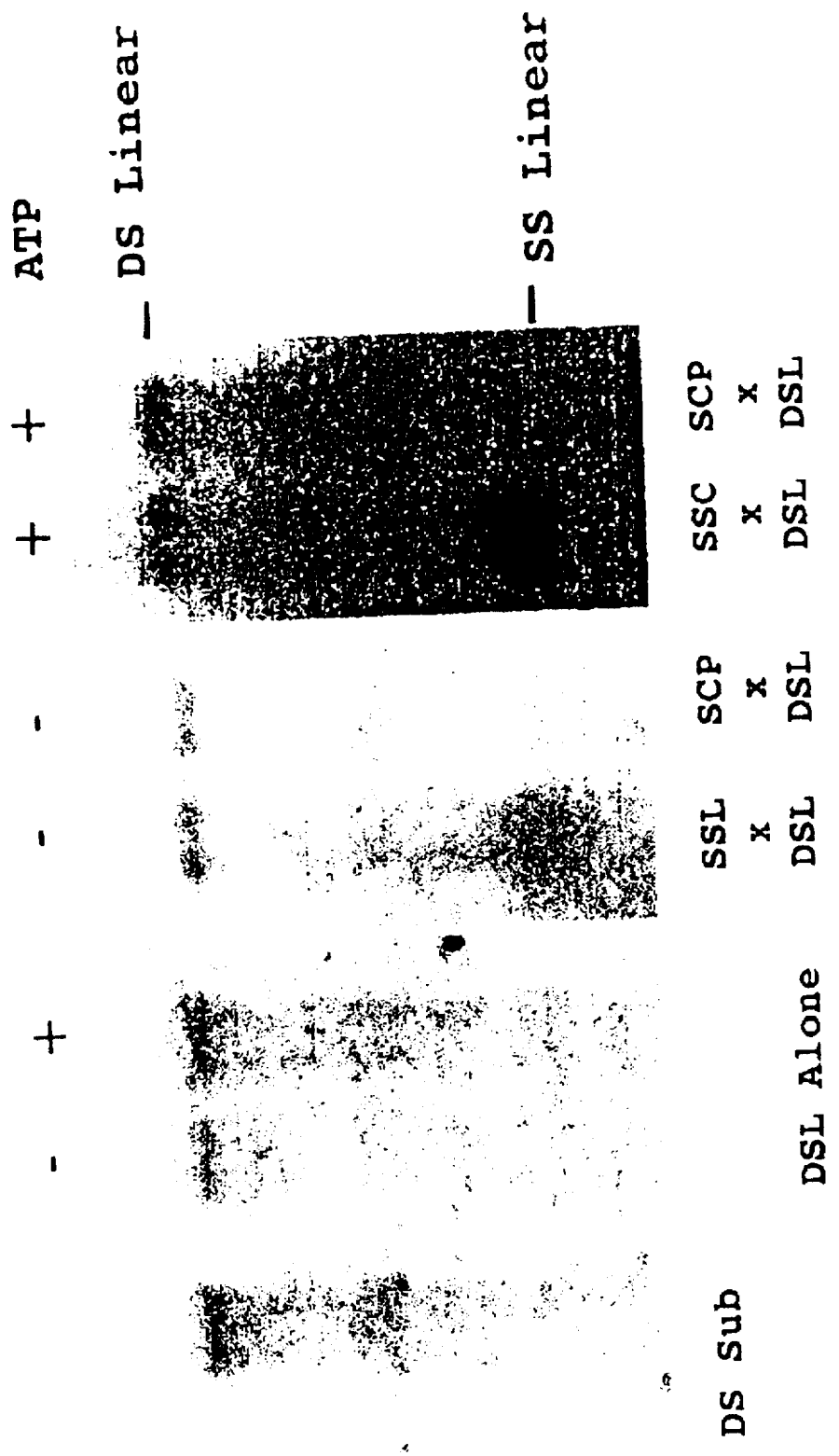
FIG. 7 depicts an ATP-dependent three strand reaction demonstrating that DRAP produces displaced strands and does not possess helicase activity. DSL is defined as double stranded linear DNA, SSC is defined as single stranded circular DNA and SCP is defined as supercoiled plasmid double stranded DNA.

End labeling of the DSL used in these same strand transfer reactions indicated that DRAP did perform strand transfer in the ATP and Mg-containing reaction. (FIG. 6F.) Before addition of SDS-containing loading dye, all the SS DNA and much of the DSL DNA were found in the protein-DNA aggregates (AG) at the top of the gel. Upon deproteinization, the label co-migrated with DSL and single stranded linear (SSL) species. Formation of the SSL product required both the SSC and DSL substrates and ATP. In addition, the SSL product was not formed from incubation of the DSL substrate alone with DRAP. (FIG. 7.)

| Standard Strand Transfer Activity Assay | | |
|---|---|---|
| | DRAP | RecA/SSB |
| DRAP (60 ng/μl) | 1 μl | |
| RecA (240 ng) | | 1 μl |
| SSB (200 ng) | | 1 μl |
| ss DNA + ds DNA (50 ng/μl, each) | 2 μl | 2 μl |
| 10 × Tris (200 mM, pH = 7.35) | 1 μl | 1 μl |
| 10 × MgCl$_2$ (50–100 mM) | 1 μl | 1 μl |
| 10 × ATP or H$_2$O (10 mM) | 1 μl | 1 μl |
| ddH$_2$O | 4 μl | 3 μl |
| | 10 μl | 10 μl |
| Incubate at 37° C. for 30 Min | | |
| Loading solution (+SDS) | 3 μl | 3 μl |
| Total μl | 13 μl | 13 μl |

Separate on a 0.8% 1×TAE agarose gel at 4–6 V/cm for 1–2 hours with ethidium bromide in the running buffer (1×TAE) or post stained and followed by photodocumentation.

Loading solution: 1×TAE, 50% glycerol, 2.5% sodium dodecylsulfate ("SDS") and bromophenol blue ("BPB").

The standard strand transfer assay experiments described above indicate that DRAP does not stop with the generation of intermediate products (JM or NC) as is observed with RecA/SSB (or RAD 51/RAD 52). The reaction with DRAP alone progresses to complete resolution of the recombination products similar to those observed when utilizing a reconstituted recombination system containing RecA/SSB with resolving endonucleases Ruv A, B and C. Thus, DRAP provides for the ability to insert or modify small pieces of single stranded or double stranded DNA directly within genes using "oligonucleotides", i.e., less than about 100 bp into the gene of interest.

B. DRAP Possesses Topoisomerase Activity

Various recombinases exhibit topoisomerase (1)—like activity. When the protein is incubated with a supercoiled plasmid one strand of the DNA is cleaved and may be religated. If the other DNA strand passes through a transient nick then the plasmid is relaxed. Nicked DNA may even be linearized. This activity is exhibited by DRAP and to a lesser extent by RecA (+ single strand binding protein, SSB). This activity is Mg—dependent but independent of ATP.

In a topoisomerase assay (see assay conditions described below), an M13mp18 plasmid preparation containing both supercoiled (SC) and nicked circular (NC) DNA forms was incubated with DRAP (60 ng) or RecA/SSB (240/200 ng) at 37° C. for 30 min. The reaction was stopped with SDS-containing loading dye and the products were separated by agarose gel electrophoresis. DRAP produced double strand linear (DSL) DNA molecules in an ATP-independent reaction to a significantly greater degree than RecA/SSB. (FIG. 6D.)

| Topoisomerase Activity Assay | DRAP | RecA/SSB |
|---|---|---|
| DRAP (60 ng/μl) | 1μl | |
| RecA (240 ng) | | 1 μl |
| SSB (200 ng) | | 1 μl |
| Plasmid (50 ng/μl) | 1 μl | 1 μl |
| 10 × Tris (200 mM, pH = 7.35) | 1 μl | 1 μl |
| 10 × MgCl₂ (50–100 mM) | 1 μl | 1 μl |
| 10 × ATP or H₂O (10 mM) | 1 μl | 1 μl |
| ddH₂O | 5 μl | 4 μl |
| | 10 μl | 10 μl |
| Incubate at 37° C. for 30 min | | |
| Loading solution (+SDS) | 3 μl | 3 μl |
| Total μl | 13 μl | 13 μl |

Separate on a 0.8% 1×TAE agarose gel at 4–6 V/cm for 1–2 hours with ethidium bromide in the running buffer (1×TAE) or post stained and followed by photo-documentation.

Loading solution, 1×TAE, 50% glycerol, 2.5% SDS, BPB

The data shown in FIG. 6D demonstrate that the presence of DRAP topoisomerase activity produced a conversion of SC to NC and NC to linear forms of DNA with the appearance of a new linear band.

C. DRAP Does Not Possess ATP-Dependent Helicase Activity

FIG. 7 shows that DRAP does not possess ATP-dependent helicase activity. The Figure shows that in a standard three strand reaction using DRAP as described in Section A above, a displaced single stranded DNA band is produced. The displacement of one strand from a labeled duplex DNA is not the consequence of an ATP-dependent helicase reaction.

The data show that no strand displacement occurred due to unwinding or helicase activity from duplex DNA incubated with DRAP, either alone or in the absence or presence of ATP. Very limited DNA displacement occurred when incubated with a homologous SSC, but no strand displacement occurred when incubated with homologous supercoiled plasmid double stranded DNA ("SCP") in the absence of ATP. Significant strand displacement from the labeled DSL DNA occurred only when a homologous SSC, but not SCP, was present and co-incubated with DRAP and ATP.

The data demonstrate that incubating DRAP with either double stranded DNA (2 strands) or double stranded and supercoiled plasmid DNA (4 strands) produces no product, while incubating double stranded and single stranded circular DNA (3 strands) provides for homologous recombination. Thus, all of the data described above demonstrate that DRAP exhibits a homology- and ATP-dependent three strand transfer activity coupled with a topoisomerase I-like ATP independent cleavage activity.

D. DRAP Does Not Possess Nuclease Activity

An assay was performed to determine if any nuclease activity, that would degrade the mutagenic oligonucleotides to be used, is present in the recombinant DRAP samples. The assay conditions are outlined below:

| Nuclease Activity Assay | |
|---|---|
| Protein Sample (60 ng/μl) | 1 μl |
| Oligonucleotide (5 ng/μl) | 1 μl |
| 10 × Tris (200 mM, pH = 7.35) | 1 μl |
| 10 × MgCl₂ (100 mM) | 1 μl |
| 10 × ATP (γ-S) (10 mM) | 1 or 0 μl |
| ddH₂O | 5 or 6 μl |
| | 10 μl |
| Incubate at 37° C. for 30 Min | |
| Loading solution (+SDS) | 3 μl |
| Total μl | 13 μl |

Separate on an 8×10 cm 6% 1×TAE minigel (MiniProtean, BioRad) at 250 V for 14 minutes. Dry gel onto filter paper and expose to film.

Loading Solution—1×TAE, 50% glycerol, BPB and xylene cyanol.

Figure 8:
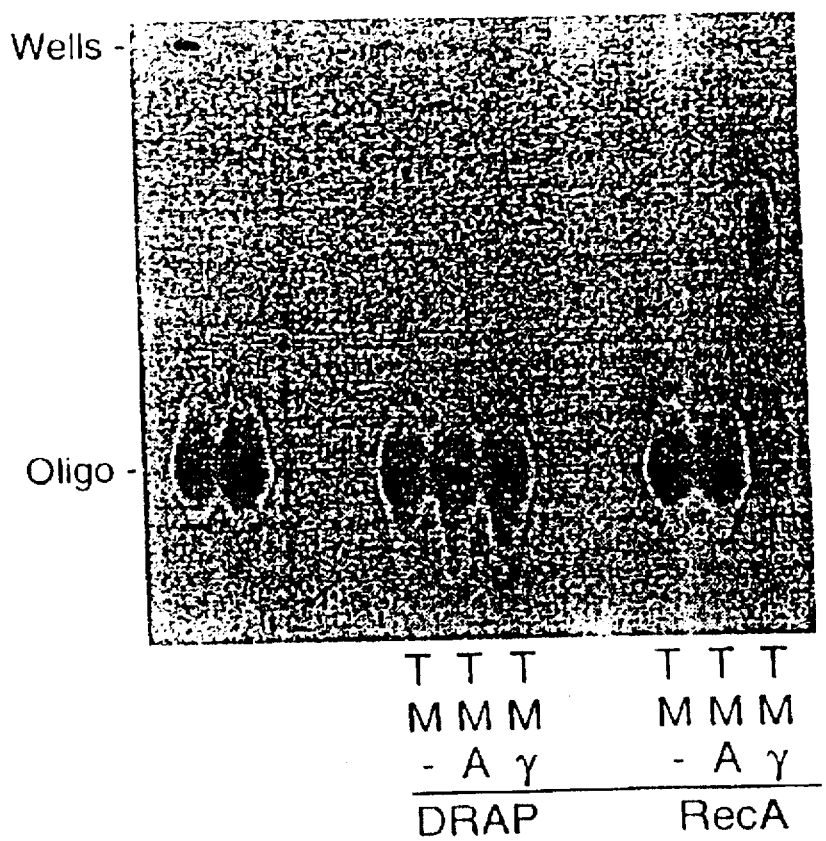
FIG. 8 depicts a polyacrylamide gel demonstrating that DRAP does not possess nuclease activity as tested with end labeled oligonucleotides.

Any oligonucleotide may be used for this assay. For this experiment, an oligonucleotide (33-mer) derived from the central portion of the pUC19 poly linker 5'-GGTACCCGGGGATCCTCTAGAGTCGACCTGCAG-3' [SEQ ID NO: 20] was endlabeled at the 5' end with ³²P-ATP using T4 polynucleotide kinase. The oligonucleotide was purified on Qiaquick columns using buffer PN (Qiagen) and the OD at 260 nm indicated a concentration of 5 ng/μl. Any oligonucleotide sequence may be used in this experiment. The SEQ ID NO: 16 oligonucleotide was incubated with 60 ng of DRAP or RecA in various buffers for 30 minutes at 37° C. A loading buffer was added and the material separated on a 6% 1×TAE, polyacrylamide minigel at 250 V for 14 minutes. The gel was dried and exposed to film with one intensifying screen for ~16 hrs. at −80° C. No degradation of the oligonucleotide was observed. (FIG. 8.) Gel shifting with RecA in the presence of ATP-γ-5 is consistent with the known properties of that protein. The data show that DRAP does not posses nuclease activity.

The data described above enable postulation of a non-limiting model of the mechanism of action of DRAP. The model is depicted in FIG. 9 and is not meant to limit the invention to this mechanism. The schematic depicted in FIG.

9 indicates how DRAP may act to couple its strand transfer and topoisomerase activities. In an ATP-independent reaction DRAP can relax and linearize a supercoiled (SC) plasmid substrate. DRAP can also form joint molecules (JM) and nicked circles (NC) from double stranded linear (DSL) and single stranded circular (SSC) substrates as is similar to RecA/SSB activity. While the reaction stops at the JM/NC stage for RecA/SSB, it progresses further for DRAP due to its topoisomerase activity. With recombinant DRAP the JMs progress completely to NCs and the NCs are converted back to DSLs. The position(s) of the cleavage(s) have not been determined and the possible putative products are indicated in FIG. 9.

Example 7
Initial Generation of Transgenic Mice

Initial transgenic experiments were carried out using DRAP and mutant oligonucleotides (mutant nucleotide is underlined and bold) corresponding to the N-myc, 5'-TTTCCTGAAAAGC<u>T</u>TATTCAGCACCCGAA-3' (Sense Strand) [SEQ ID NO: 21]; β-1 Globin, 5'-ATGGTGCACCTGACTGATG<u>T</u>TGAGAAG-3' (Sense Strand) [SEQ ID NO: 22]; and Agouti genes. (See FIG. 11.)

The amount of olignucleotide DNA for the injections was based upon estimates of the number of "gene-sized" DNA molecules injected in a routine transgenic experiment. It was estimated that approximately 500 molecules per picoliter ("pl") were injected in a typical transgenic experiment. This translates to a concentration of approximately 7.5 ng/ml for a 30-mer oligomer. In a preferred embodiment, the mutagenic oligonucleotide used should be hydroxylated at the 5' end ("5'OH").

Three different ratios of protein per nucleotide were examined for each of the co-injections. The "Low" ratio was equal to 1 protein molecule for each oligonucleotide. The "Medium" ratio was consistent with the observed ratio for RecA of 1 protein molecule for every three nucleotides (10 protein molecules/30-mer). The "High" ratio was one factor of ten above the observed value for RecA which gave a final ratio of 100 protein molecules per 30-mer. There was no observed toxicity to the embryos at any of the co-injection ratios.

As seen in FIG. 11, phenotypic changes were observed with the "High" ratio. The still-born phenotype for N-myc targeting is consistent with an embryonic lethal, i.e., a conventional "knockout". The runt phenotype for β1-globin targeting is consistent with a potential change in oxygen carrying capacity of β or highly homologous globins in mice during embryonic and/or fetal development. Thus this ratio of protein to oligonucleotide was the starting point for all further transgenic studies. The toxicity to the embryo of increasing the amount of DNA and/or protein should also be determined prior to reimplantation of injected zygotes. The data for these experiments is provided in FIG. 11. That data show that experiments utilizing 5'OH-containing oligomers directed to the N-myc Exon1 and β1-globin genes produced phenotypically transgenic mice, while mice generated with the Agouti 5'OH oligomer produced no obvious phenotypic change.

It was determined through restriction analysis of DNA from multiple animals that a direct replacement of the N-myc and β1-globin loci did not occur.

Example 8
Additional Transgenic Experiment
Selection of Additional Target Gene

The mouse genetic database was examined for candidate genes in order to test the ability of DRAP to produce targeted mutations in transgenic mice. The criteria for inclusion were:

1. The method should be able to reproduce a known point mutation.
2. The known mutation should be associated with an observable phenotype that is easily confirmed by molecular methods.
3. The mutation/phenotype should be autosomal dominant or semi-dominant.
4. The mutation/phenotype should not be lethal even when homozygous.

Using these criteria, the c-Kit tyrosine kinase receptor was selected.

Mutations in this gene are responsible for the white spotting phenotype. The best allele for mutagenesis is W-42. This missense mutation produces a Restriction Fragment Length Polymorphism (RFLP) that is capable of being evaluated by cleavage of a PCR product. Furthermore, there are only a few related sequences in the data base with similarity to the proposed mutagenic oligonucleotide.

The portion of the gene that was determined to be suitable for modification along with the new RFLPs that would be generated are shown in FIGS. 12A–B. Because coat color variation is readily apparent and can be demonstrated in a photographic record, we attempted to modify the c-kit gene with a mutagenic oligonucleotide.

Injection of DRAP and c-kit Oligos

DRAP was coinjected into male pronuclei of fertilized mouse eggs with c-kit 5'P-containing oligonucleotide, [SEQ ID NO:9] at a concentration of 10:1 molar ratio of DRAP to oligonucleotide. In this experiment approximately 500,000 molecules of DRAP and approximately 50,000 molecules of oligonucleotide per embryo were injected using the standard transgenic protocol as described in U.S. Pat. No. 4,873,191.

Analysis of the transgenic animals for the mutant c-kit are carried out at two levels.

Figure 13A:
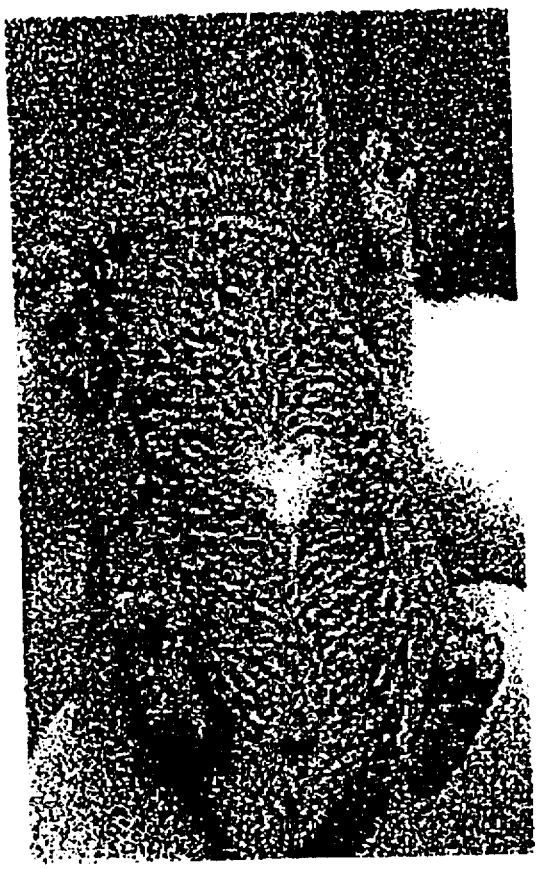
FIGS. 13A–B depicts a photograph of a white spotted mouse produced from the co-injection of DRAP (A) and the mutagenic c-kit oligonucleotide and a photograph of an unspotted control mouse (B).
Figure 13B:

The first level of analysis is to assess for visual evidence of the white spotting phenotype. FIG. 13A depicts a photograph of a white spotted mouse produced from the co-injection of DRAP and the mutagenic c-kit oligonucleotide as well as an unspotted control mouse. The data depict a disruption of the wild type gene sufficient to alter the gene product of the embryo, ablate gene function and produce the expected white-spotted phenotype.

The second level of analysis is to perform molecular analysis of the c-kit gene for evidence of a gene conversion event. The molecular analysis is performed by genomic DNA PCR amplification of either the complete or a partial fragment from exon 17 utilizing the PCR probes identified as [SEQ ID NO:9 and 10]. This is followed by determining if the new Apo I or Tsp 509 1 restriction sites are created in the gene conversion event. Because the exon size is small (124 bp) and the cleavage is near one end of the fragment, the restriction products are to be separated on a 6% polyacrylamide gel.

For restriction analysis Tsp5091 is, perhaps, the better choice of enzyme to use because Apo I is subject to "star" activity. Star activity could lead to false positive results. For final confirmation, the PCR material can be cloned into a standard vector and then sequenced. All of the critical enzymes needed are commercially available (NEB and others).

All of the references identified hereinabove, are hereby expressly incorporated herein by reference to the extent that they describe, set forth, provide a basis for or enable compositions and/or methods which may be important to the practice of one or more embodiments of the present inventions.

What is claimed is:

1. An isolated first nucleic acid that hybridizes to a second nucleic under high stringency hybridization conditions, wherein said second nucleic acid comprises a sequence selected from the group consisting of SEQ ID NO: 1, SEQ ID NO: 2 and SEQ ID NO: 3, and said isolated first nucleic acid encodes a polypeptide with recombinase and topoisomerase activities.

2. An isolated nucleic acid comprising an isolated first nucleic acid that is a deoxyribonucleic acid that:
   (a) hybridizes under high stringency hybridization conditions to a second nucleic acid comprising a sequence selected from the group consisting of SEQ ID NO: 1, SEQ ID NO: 2 and SEQ ID NO: 3; and
   (b) encodes a polypeptide comprising recombinase and topoisomerase activities.

* * * * *

Disclaimer

6,858,716 B2—EISEN, Andrew, Rockville, Md. (US). DROSOPHILA RECOMBINATION-ASSOCIATED PROTEIN AND METHODS FOR USE. Patent dated February 22, 2005. Disclaimer filed January 28, 2003, by the Inventor.

Hereby disclaims the terminal part of any patent granted on the above-identified application, which would extend beyond the expiration date of the full statutory term of U.S. Patent No. 6,534,643.

*(Official Gazette, July 26, 2005)*

SEQUENCE LISTING

<160> NUMBER OF SEQ ID NOS: 35
<210> SEQ ID NO 1
<211> LENGTH: 1378
<212> TYPE: DNA
<213> ORGANISM: Drosophila melanogaster

<400> SEQUENCE: 1

| | | | | | | |
|---|---|---|---|---|---|---|
| agcgattacg | gtagagatat | ggtaatgcaa | cggtggatgt | gaactccttg | gtttgcggtg | 60 |
| aatgcgttca | acggtggatc | ttcgcttgca | cctttcgcga | tagacgacat | acggatacag | 120 |
| atacagatac | agaatggcct | ccaacaacag | tagtaccacc | gatctggaca | gccaggtcaa | 180 |
| tgtggaggat | ttgcccataa | cgttcaaggt | gaagtacatt | ggttccgaag | tggcacgtgg | 240 |
| cttatggggc | attaagtata | cgcgtcgtcc | ggttgacata | atggtgggcg | tggccaagaa | 300 |
| cctgccgccc | aataaggtgc | tgcccaactg | cgaactgaag | gtgtccaccg | acggagtcca | 360 |
| gctggagatc | atatcgccaa | aggccagcat | caatcactgg | agctatccca | tcgacacgat | 420 |
| ctcgtatggc | gttcaggacc | tggtctacac | aagggtcttt | gccatgatcg | tggtgaagga | 480 |
| cgagtcgagt | ccgcatccct | tgaggttca | cgccttcgtg | tgcgacagtc | gtgcgatggc | 540 |
| gcggaagttg | acctttgccc | tggccggccg | ccttccagga | ttactcgcga | cgggtcaagg | 600 |
| aggcaaccgg | tgaggaggag | ggcgaggcca | cgcccagcga | cactattaca | cccacgcgac | 660 |
| acaagttcgc | catcgatctg | cgaacgccgg | agaaatccag | gctggcgaac | tggagcagga | 720 |
| aacggaggcg | tagttatcct | ggtgatcctg | cgttggctcc | gtcaatgaga | tgtgatgtgt | 780 |
| tagttactta | acgtccagtg | ttcactgtat | ctgtaaattg | tggttctctc | acctggtagt | 840 |
| tgcctcatac | agctaattac | ccaaagccta | agtgttaata | cgatttgtaa | acgatttcta | 900 |
| aaataaatta | cgaatatggt | atgtttggct | atttgaattg | ggctacaacc | tgttgatatg | 960 |
| ccacttggca | aaaaaaaaaa | acgccagcac | caattctttt | acttctgttt | cttgtgaccg | 1020 |
| acataaaaga | tgcaccaaag | ctgctattcc | accagcgttc | tttattccac | gcttgttttc | 1080 |
| atcattttgt | cttccgtaag | ataaattacg | taaagcacca | caggcatttt | tatgtatttc | 1140 |
| tggagaatca | taagatagca | gtcgaactaa | tggtggtata | cctcccagag | atcttgtacg | 1200 |
| ttgcttgttt | ggatcatcca | tgtagcacaa | atgctgtaga | taggctgctg | cattagcttt | 1260 |
| tatagcacta | ctcgggttgc | ttaaaaagct | tattacttct | gaaagatttg | gatcccgcca | 1320 |
| tctcattgta | gaacaaatat | cattttctga | tccttcaatg | taatcatcct | tttcttcc | 1378 |

<210> SEQ ID NO 2
<211> LENGTH: 477
<212> TYPE: DNA
<213> ORGANISM: Drosophila melanogaster

<400> SEQUENCE: 2

| | | | | | | |
|---|---|---|---|---|---|---|
| atggcctcca | acaacagtag | taccaccgat | ctggacagcc | aggtcaatgt | ggaggatttg | 60 |
| cccataacgt | tcaaggtgaa | gtacattggt | tccgaagtgg | cacgtggctt | atggggcatt | 120 |
| aagtatacgc | gtcgtccggt | tgacataatg | gtgggcgtgg | ccaagaacct | gccgcccaat | 180 |
| aaggtgctgc | ccaactgcga | actgaaggtg | tccaccgacg | gagtccagct | ggagatcata | 240 |
| tcgccaaagg | ccagcatcaa | tcactggagc | tatcccatcg | acacgatctc | gtatggcgtt | 300 |
| caggacctgg | tctacacaag | ggtctttgcc | atgatcgtgg | tgaaggacga | gtcgagtccg | 360 |
| catcccttg | aggttcacgc | cttcgtgtgc | gacagtcgtg | cgatggcgcg | gaagttgacc | 420 |

```
tttgccctgg ccggccgcct tccaggatta ctcgcgacgg gtcaaggagg caaccgg        477
```

<210> SEQ ID NO 3
<211> LENGTH: 507
<212> TYPE: DNA
<213> ORGANISM: Drosophila melanogaster

<400> SEQUENCE: 3

```
acgacatacg gatacagata cagatacaga atggcctcca acaacagtag taccaccgat     60
ctggacagcc aggtcaatgt ggaggatttg cccataacgt tcaaggtgaa gtacattggt    120
tccgaagtgg cacgtggctt atggggcatt aagtatacgc gtcgtccggt tgacataatg    180
gtgggcgtgg ccaagaacct gccgcccaat aaggtgctgc ccaactgcga actgaaggtg    240
tccaccgacg gagtccagct ggagatcata tcgccaaagg ccagcatcaa tcactggagc    300
tatcccatcg acacgatctc gtatggcgtt caggacctgg tctacacaag ggtctttgcc    360
atgatcgtgg tgaaggacga gtcgagtccg catcccttg aggttcacgc cttcgtgtgc    420
gacagtcgtg cgatggcgcg gaagttgacc tttgccctgg ccggccgcct tccaggatta    480
ctcgcgacgg gtcaaggagg caaccgg                                        507
```

<210> SEQ ID NO 4
<211> LENGTH: 159
<212> TYPE: PRT
<213> ORGANISM: Drosophila melanogaster

<400> SEQUENCE: 4

```
Met Ala Ser Asn Asn Ser Ser Thr Thr Asp Leu Asp Ser Gln Val Asn
1               5                   10                  15

Val Glu Asp Leu Pro Ile Thr Phe Lys Val Lys Tyr Ile Gly Ser Glu
            20                  25                  30

Val Ala Arg Gly Leu Trp Gly Ile Lys Tyr Thr Arg Arg Pro Val Asp
        35                  40                  45

Ile Met Val Gly Val Ala Lys Asn Leu Pro Pro Asn Lys Val Leu Pro
    50                  55                  60

Asn Cys Glu Leu Lys Val Ser Thr Asp Gly Val Gln Leu Glu Ile Ile
65                  70                  75                  80

Ser Pro Lys Ala Ser Ile Asn His Trp Ser Tyr Pro Ile Asp Thr Ile
                85                  90                  95

Ser Tyr Gly Val Gln Asp Leu Val Tyr Thr Arg Val Phe Ala Met Ile
            100                 105                 110

Val Val Lys Asp Glu Ser Ser Pro His Pro Phe Glu Val His Ala Phe
        115                 120                 125

Val Cys Asp Ser Arg Ala Met Ala Arg Lys Leu Thr Phe Ala Leu Ala
    130                 135                 140

Gly Arg Leu Pro Gly Leu Leu Ala Thr Gly Gln Gly Gly Asn Arg
145                 150                 155
```

<210> SEQ ID NO 5
<211> LENGTH: 6
<212> TYPE: PRT
<213> ORGANISM: Drosophila melanogaster
<220> FEATURE:
<221> NAME/KEY: misc_feature
<223> OTHER INFORMATION: Antigenic peptide

<400> SEQUENCE: 5

```
Lys Asp Glu Ser Ser Pro
1               5
```

```
<210> SEQ ID NO 6
<211> LENGTH: 6
<212> TYPE: PRT
<213> ORGANISM: Drosophila melanogaster
<220> FEATURE:
<221> NAME/KEY: misc_feature
<223> OTHER INFORMATION: Antigenic peptide

<400> SEQUENCE: 6

Thr Arg Arg Pro Val Asp
1               5

<210> SEQ ID NO 7
<211> LENGTH: 6
<212> TYPE: PRT
<213> ORGANISM: Drosophila melanogaster
<220> FEATURE:
<221> NAME/KEY: misc_feature
<223> OTHER INFORMATION: Antigenic peptide

<400> SEQUENCE: 7

Arg Ala Met Ala Arg Lys
1               5

<210> SEQ ID NO 8
<211> LENGTH: 130
<212> TYPE: DNA
<213> ORGANISM: Mus musculus

<400> SEQUENCE: 8
ggacagtgta ttcacagaga tttggcagcc aggaatatcc tcctcactca cgggcggatc      60
acaaagattt gcgatttcgg gctagccaga gacatcagga atgattcgaa ttacgtggtc     120
aaaggaaatg                                                            130

<210> SEQ ID NO 9
<211> LENGTH: 37
<212> TYPE: DNA
<213> ORGANISM: Artificial Sequence
<220> FEATURE:
<223> OTHER INFORMATION: murine c-kit Exon 17 mutagenic oligonucleotide

<400> SEQUENCE: 9
ggacagtgta ttcacagaga tttggcagcc aggaata                               37

<210> SEQ ID NO 10
<211> LENGTH: 15
<212> TYPE: DNA
<213> ORGANISM: Mus musculus
<220> FEATURE:
<221> NAME/KEY: misc_feature
<223> OTHER INFORMATION: Primer

<400> SEQUENCE: 10
ggacagtgta ttcac                                                       15

<210> SEQ ID NO 11
<211> LENGTH: 17
<212> TYPE: DNA
<213> ORGANISM: Mus musculus
<220> FEATURE:
<221> NAME/KEY: misc_feature
<223> OTHER INFORMATION: Primer

<400> SEQUENCE: 11
ttgcgatttc gggctag                                                     17
```

-continued

```
<210> SEQ ID NO 12
<211> LENGTH: 57
<212> TYPE: DNA
<213> ORGANISM: Mus musculus

<400> SEQUENCE: 12
tgtattcaca gaaatttggc agccaggaat atcctcactc acgggcggat cacaaag        57

<210> SEQ ID NO 13
<211> LENGTH: 41
<212> TYPE: PRT
<213> ORGANISM: Mus musculus

<400> SEQUENCE: 13

Cys Ile His Arg Asp Leu Ala Ala Arg Asn Ile Leu Leu Thr His Gly
 1               5                  10                  15

Arg Ile Thr Lys Ile Cys Asp Phe Gly Leu Ala Arg Asp Ile Arg Asn
            20                  25                  30

Asp Ser Asn Tyr Val Val Lys Gly Asn
        35                  40

<210> SEQ ID NO 14
<211> LENGTH: 20
<212> TYPE: PRT
<213> ORGANISM: Mus musculus

<400> SEQUENCE: 14

Cys Ile His Arg Asn Leu Ala Ala Arg Asn Ile Leu Leu Thr His Gly
 1               5                  10                  15

Arg Ile Thr Lys
            20

<210> SEQ ID NO 15
<211> LENGTH: 10
<212> TYPE: PRT
<213> ORGANISM: Drosophila melanogaster
<220> FEATURE:
<221> NAME/KEY: misc feature
<223> OTHER INFORMATION: Peptide motif

<400> SEQUENCE: 15

Met Ile Val Val Lys Asp Glu Ser Ser Pro
 1               5                  10

<210> SEQ ID NO 16
<211> LENGTH: 6
<212> TYPE: PRT
<213> ORGANISM: Drosophila melanogaster
<220> FEATURE:
<221> NAME/KEY: misc_feature
<223> OTHER INFORMATION: N-myristylation site

<400> SEQUENCE: 16

Gly Ser Glu Val Ala Arg
 1               5

<210> SEQ ID NO 17
<211> LENGTH: 6
<212> TYPE: PRT
<213> ORGANISM: Drosophila melanogaster
<220> FEATURE:
<221> NAME/KEY: misc_feature
<223> OTHER INFORMATION: N-myristylation site
```

-continued

<400> SEQUENCE: 17

Gly Ile Lys Tyr Thr Arg
1               5

<210> SEQ ID NO 18
<211> LENGTH: 6
<212> TYPE: PRT
<213> ORGANISM: Drosophila melanogaster
<220> FEATURE:
<221> NAME/KEY: misc_feature
<223> OTHER INFORMATION: N-myristylation site

<400> SEQUENCE: 18

Gly Val Ala Lys Asn Leu
1               5

<210> SEQ ID NO 19
<211> LENGTH: 6
<212> TYPE: PRT
<213> ORGANISM: Drosophila melanogaster
<220> FEATURE:
<221> NAME/KEY: misc_feature
<223> OTHER INFORMATION: N-myristylation site

<400> SEQUENCE: 19

Gly Leu Leu Ala Thr Gly
1               5

<210> SEQ ID NO 20
<211> LENGTH: 33
<212> TYPE: DNA
<213> ORGANISM: Artificial Sequence
<220> FEATURE:
<223> OTHER INFORMATION: pUC19 poly linker

<400> SEQUENCE: 20
ggtacccggg gatcctctag agtcgacctg cag                          33

<210> SEQ ID NO 21
<211> LENGTH: 29
<212> TYPE: DNA
<213> ORGANISM: Artificial Sequence
<220> FEATURE:
<223> OTHER INFORMATION: Murine N-myc mutagenic oligonucleotide

<400> SEQUENCE: 21
tttcctgaaa agcttattca gcacccgaa                               29

<210> SEQ ID NO 22
<211> LENGTH: 27
<212> TYPE: DNA
<213> ORGANISM: Artificial Sequence
<220> FEATURE:
<223> OTHER INFORMATION: Murine beta-1-globin mutagenic oligonucleotide

<400> SEQUENCE: 22
atggtgcacc tgactgatgt tgagaag                                 27

<210> SEQ ID NO 23
<211> LENGTH: 6
<212> TYPE: PRT
<213> ORGANISM: Mus musculus
<220> FEATURE:
<221> NAME/KEY: misc_feature
<223> OTHER INFORMATION: Peptide motif -continued

```
<400> SEQUENCE: 23

Leu Leu Ile Val Asp Ser
1               5

<210> SEQ ID NO 24
<211> LENGTH: 6
<212> TYPE: PRT
<213> ORGANISM: Saccharomyces cerevisiae
<220> FEATURE:
<221> NAME/KEY: misc_feature
<223> OTHER INFORMATION: peptide motif

<400> SEQUENCE: 24

Leu Ile Val Val Asp Ser
1               5

<210> SEQ ID NO 25
<211> LENGTH: 6
<212> TYPE: PRT
<213> ORGANISM: Escherichia coli
<220> FEATURE:
<221> NAME/KEY: misc_feature
<223> OTHER INFORMATION: Peptide motif

<400> SEQUENCE: 25

Val Ile Val Val Asp Ser
1               5

<210> SEQ ID NO 26
<211> LENGTH: 10
<212> TYPE: PRT
<213> ORGANISM: Saccharomyces cerevisiae
<220> FEATURE:
<221> NAME/KEY: misc_feature
<223> OTHER INFORMATION: Peptide motif

<400> SEQUENCE: 26

Met Ile Ala Leu Lys Asp Glu Thr Asn Pro
1               5                   10

<210> SEQ ID NO 27
<211> LENGTH: 10
<212> TYPE: PRT
<213> ORGANISM: Bacteriophage T4
<220> FEATURE:
<221> NAME/KEY: misc_feature
<223> OTHER INFORMATION: Peptide motif

<400> SEQUENCE: 27

Ile Leu Val Val Lys Asp Pro Ala Ala Pro
1               5                   10

<210> SEQ ID NO 28
<211> LENGTH: 10
<212> TYPE: PRT
<213> ORGANISM: Bacteriophage T4
<220> FEATURE:
<221> NAME/KEY: misc_feature
<223> OTHER INFORMATION: Peptide motif

<400> SEQUENCE: 28

Met Ile Ala Val Asp Val Glu Met Gly Glu
1               5                   10
```

```
<210> SEQ ID NO 29
<211> LENGTH: 6
<212> TYPE: PRT
<213> ORGANISM: Bacteriophage T4
<220> FEATURE:
<221> NAME/KEY: misc_feature
<223> OTHER INFORMATION: Peptide motif

<400> SEQUENCE: 29

Lys Gly Phe Ser Ser Glu
1               5

<210> SEQ ID NO 30
<211> LENGTH: 5
<212> TYPE: PRT
<213> ORGANISM: Homo sapiens
<220> FEATURE:
<221> NAME/KEY: misc_feature
<223> OTHER INFORMATION: Peptide motif

<400> SEQUENCE: 30

Ile Lys Asp Glu Pro
1               5

<210> SEQ ID NO 31
<211> LENGTH: 6
<212> TYPE: PRT
<213> ORGANISM: Homo sapiens
<220> FEATURE:
<221> NAME/KEY: misc_feature
<223> OTHER INFORMATION: Peptide motif

<400> SEQUENCE: 31

Lys Asp Gly Ser Ser Glu
1               5

<210> SEQ ID NO 32
<211> LENGTH: 5
<212> TYPE: PRT
<213> ORGANISM: Homo sapiens
<220> FEATURE:
<221> NAME/KEY: misc_feature
<223> OTHER INFORMATION: Peptide motif

<400> SEQUENCE: 32

Gly Phe Ser Ser Pro
1               5

<210> SEQ ID NO 33
<211> LENGTH: 4
<212> TYPE: PRT
<213> ORGANISM: Drosophila melanogaster
<220> FEATURE:
<221> NAME/KEY: MISC_FEATURE
<223> OTHER INFORMATION: Potential N-glycosylation site

<400> SEQUENCE: 33

Asn Asn Ser Ser
1

<210> SEQ ID NO 34
<211> LENGTH: 4
<212> TYPE: PRT
<213> ORGANISM: Drosophila melanogaster
<220> FEATURE:
<221> NAME/KEY: MISC_FEATURE
<223> OTHER INFORMATION: Potential phosphorylation site
```

-continued

```
<400> SEQUENCE: 34

Arg Lys Leu Thr
1

<210> SEQ ID NO 35
<211> LENGTH: 4
<212> TYPE: PRT
<213> ORGANISM: Drosophila melanogaster
<220> FEATURE:
<221> NAME/KEY: MISC FEATURE
<223> OTHER INFORMATION: Potential phosphorylation site

<400> SEQUENCE: 35

Ser Thr Thr Asp
1
```